United States Patent
Kubota et al.

(10) Patent No.: US 7,560,604 B2
(45) Date of Patent: Jul. 14, 2009

(54) BIPHENYL DERIVATIVE, MATERIAL FOR ORGANIC ELECTROLUMINESCENCE DEVICE, AND ORGANIC ELECTROLUMINESCENCE DEVICE USING THE SAME

(75) Inventors: Mineyuki Kubota, Chiba (JP); Mitsunori Ito, Chiba (JP); Chishio Hosokawa, Chiba (JP);

(73) Assignee: Idemitsu Kosan Co., Ltd., Tokyo (JP)

( * ) Notice: Subject to any disclaimer, the term of this patent is extended or adjusted under 35 U.S.C. 154(b) by 300 days.

(21) Appl. No.: 11/481,820

(22) Filed: Jul. 7, 2006

(65) Prior Publication Data

US 2007/0013296 A1  Jan. 18, 2007

(30) Foreign Application Priority Data

Jul. 14, 2005 (JP) ............................ 2005-205522

(51) Int. Cl.
  *C07C 15/20* (2006.01)
  *H01L 51/54* (2006.01)
  *C07F 7/08* (2006.01)
(52) U.S. Cl. .................. 585/26; 428/690; 313/504; 313/506; 257/102; 257/E51.049
(58) Field of Classification Search ................ 428/690, 428/197; 313/504, 506; 257/40, E51.044, 257/102, E51.049; 585/24–26
See application file for complete search history.

(56) References Cited

U.S. PATENT DOCUMENTS

| 6,635,364 | B1 | 10/2003 | Igarashi |
| 2002/0177009 | A1 | 11/2002 | Suzuki et al. |
| 2003/0044640 | A1* | 3/2003 | Funahashi et al. ........... 428/690 |
| 2004/0263067 | A1* | 12/2004 | Saitoh et al. ................ 313/504 |
| 2005/0048318 | A1 | 3/2005 | Suzuki et al. |
| 2005/0064240 | A1 | 3/2005 | Mishima et al. |
| 2005/0099115 | A1* | 5/2005 | Saitoh et al. ................ 313/504 |

FOREIGN PATENT DOCUMENTS

| CN | 1791567 A | 6/2006 |
| EP | 1491609 A2 | 12/2004 |
| EP | 1 623 968 A1 | 2/2006 |
| EP | 1 659 129 A1 | 5/2006 |
| JP | 3-200889 | 9/1991 |
| JP | 7-138561 | 5/1995 |
| JP | 8-12600 | 1/1996 |
| JP | 8-239655 | 9/1996 |
| JP | 11-3782 | 1/1999 |
| JP | 2000-182776 | 6/2000 |
| JP | 2000-344691 | 12/2000 |
| JP | 2001-192651 | 7/2001 |
| JP | 2001-257074 | 9/2001 |
| JP | 2002-329580 | 11/2002 |
| JP | 2004-2351 | 1/2004 |
| JP | 2004-339136 | 12/2004 |
| JP | 2005-15418 | 1/2005 |
| JP | 2005-15420 | 1/2005 |
| JP | 2005-112784 | 4/2005 |
| JP | 2005-123164 | 5/2005 |
| JP | 2005-222751 | 8/2005 |
| WO | WO 2004/110968 A1 | 12/2004 |
| WO | WO 2005/033118 A1 | 4/2005 |

OTHER PUBLICATIONS

C.W. Tang, et al., "Organic electroluminescent diodes", Appl. Phys. Lett. vol. 51, No. 12, Sep. 21, 1987, pp. 913-915.

* cited by examiner

*Primary Examiner*—Callie E Shosho
*Assistant Examiner*—Michael Wilson
(74) *Attorney, Agent, or Firm*—Oblon, Spivak, McClelland, Maier & Neustadt, P.C.

(57) ABSTRACT

A biphenyl derivative having a specific structure and an organic electroluminescent device having a long lifetime due to comprising at least one of organic thin film layers including a light emitting layer sandwiched between a pair of electrodes consisting of an anode and a cathode, wherein the organic thin film layer contains the biphenyl derivatives, singly or as a component of a mixture are provided, and also the biphenyl derivatives particularly suitable for a light emitting material of the organic EL device of the present invention is provided.

19 Claims, No Drawings

BIPHENYL DERIVATIVE, MATERIAL FOR ORGANIC ELECTROLUMINESCENCE DEVICE, AND ORGANIC ELECTROLUMINESCENCE DEVICE USING THE SAME

TECHNICAL FIELD

The present invention relates to a biphenyl derivative having a specific structure and an organic electroluminescence device using the biphenyl derivative as a light emitting layer, and in particular, to an organic electroluminescence device having a long lifetime, and also to the biphenyl derivative for realizing the organic electroluminescence device.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-quinolinolato)aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that excitons formed in the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

In addition, as the light emitting material of the organic EL device, chelate complexes such as tris(8-quinolinolato)aluminum, coumarine derivatives, tetraphenylbutadiene derivatives, bisstyrylarylene derivatives and oxadiazole derivatives are known. It is reported that light in the visible region ranging from a blue light to a red light can be obtained by using these light emitting materials, and development of a device exhibiting color images is expected (refer to, for example, Patent literatures 1, 2 and 3).

Further, devices including phenyl anthracene derivatives as a light emitting material were disclosed in Patent literature 4. Materials having naphthyl groups at the 9th and 10th positions of anthracene were disclosed in Patent literature 5. Although such anthracene derivatives were employed as a material for emitting a blue light, it has been desired to improve a lifetime of the devices.

In addition, materials having fluoranthene groups at the 9th and 10th positions of anthracene were disclosed in Patent literature 6. Although such anthracene derivatives were employed as a material for emitting a blue light, it has been desired to improve a lifetime of the devices.

Further, it was disclosed to employ a variety of anthracene derivatives as a hole transporting material in Patent literature 7. However, they have not yet been evaluated as a light emitting material.

Meanwhile, benzene derivatives having three substituent were disclosed in Patent literature 8, and bisanthracene derivatives were disclosed in Patent literatures 9 to 12. Although these derivatives were employed as a material for emitting a blue light and exhibited high heat resistance due to its high glass transition temperature, it has been desired to improve a lifetime of the devices.

[Patent literature 1] Japanese Patent Application Laid-Open No. Heisei 8(1996)-239655
[Patent literature 2] Japanese Patent Application Laid-Open No. Heisei 7(1995)-138561
[Patent literature 3] Japanese Patent Application Laid-Open No. Heisei 3(1991)-200889
[Patent literature 4] Japanese Patent Application Laid-Open No. Heisei 8(1996)-12600
[Patent literature 5] Japanese Patent Application Laid-Open No. Heisei 11(1991)-3782
[Patent literature 6] Japanese Patent Application Laid-Open No. 2001-257074
[Patent literature 7] Japanese Patent Application Laid-Open No. 2000-182776
[Patent literature 8] Japanese Patent Application Laid-Open No. 2001-192651
[Patent literature 9] Japanese Patent Application Laid-Open No. Heisei 8(1996)-12600
[Patent literature 10] Japanese Patent Application Laid-Open No. 2000-344691
[Patent literature 11] Japanese Patent Application Laid-Open No. 2004-2351
[Patent literature 12] Japanese Patent Application Laid-Open No. 2005-15420

The present invention has been made to overcome the above problems and has an objective of providing an organic EL device having a long lifetime. In addition, the present invention has an objective of providing a biphenyl derivative, which is particularly suitable as a light emitting material for the organic EL device of the present invention.

As a result of intensive researches and studies to achieve the above objective by the present inventors, it was found that it was possible to fabricate an organic EL device having a long lifetime by employing the biphenyl derivatives represented by the general formula (I) as a material for an organic EL device:

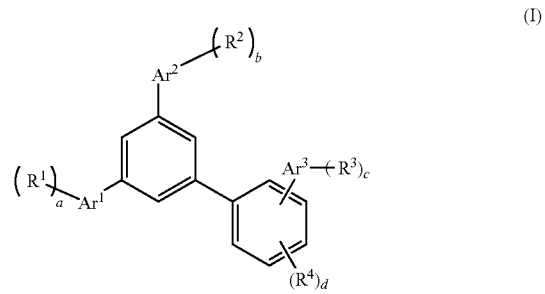

In the general formula (I), $Ar^1$ and $Ar^2$ represent a condensed aromatic hydrocarbon group comprising 3 rings or more, and $Ar^3$ represents a phenyl group or a condensed aromatic hydrocarbon group comprising 2 rings or more.

However, when one of $Ar^1$ to $Ar^3$ represents an anthracene-9-yl group, 10th position of anthracene is not a hydrogen atom.

$R^1$ to $R^3$ each independently represents, a substituted or unsubstituted aromatic hydrocarbon group having ring carbon atoms of 6 to 50, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having ring carbon atoms of 7 to 50, a substituted or unsubstituted aryloxy group having ring carbon atoms of 6 to 50, a substituted or unsubstituted arylthio group having ring carbon atoms of 6 to 50, a substituted or unsubstituted alkoxycarbonyl group having carbon atoms of 2 to 50, a silyl group, which may be substituted with a substituted or unsubstituted alkyl group having carbon atoms of 1 to 50 or a substituted or unsubstituted aryl group having ring carbon atoms of 6 to 50, a carboxyl group, a halogen atom, a cyano group, a nitro group, or a hydroxy group.

$R^4$ represents, a substituted or unsubstituted aromatic hydrocarbon group having ring carbon atoms of 6 to 10, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 7 to 50, a substituted or unsubstituted aryloxy group having carbon atoms of 6 to 50, a substituted or unsubstituted arylthio group having carbon atoms of 6 to 50, a substituted or unsubstituted alkoxycarbonyl group having carbon atoms of 2 to 50, a silyl group which may be substituted with a substituted or unsubstituted alkyl group having carbon atoms of 1 to 50 or a substituted or unsubstituted aryl group having ring carbon atoms of 6 to 50, a carboxyl group, a halogen atom, a cyano group, a nitro group, or a hydroxy group.

a to d each independently represents an integer of 0 to 3.

The present invention provides an organic EL device comprising single or a plurality of organic thin film layers including at least a light emitting layer sandwiched between a pair of electrode consisting of an anode and a cathode, wherein at least one layer of the organic thin film layers contains the aforementioned biphenyl derivatives.

The present invention has been made to overcome the above problems and can provide an organic EL device having a long lifetime. Further, it is possible to provide a particularly suitable biphenyl derivative, which has an adequate long lifetime as a material for an organic EL device of the present invention.

THE PREFERRED EMBODIMENT TO CARRY OUT THE INVENTION

The first invention of the present inventions relates to the biphenyl derivatives represented by the following formula (I). The following formulae (II) and (III) are particularly preferable for the general formula (I), and the formula (III) is more particularly preferable,

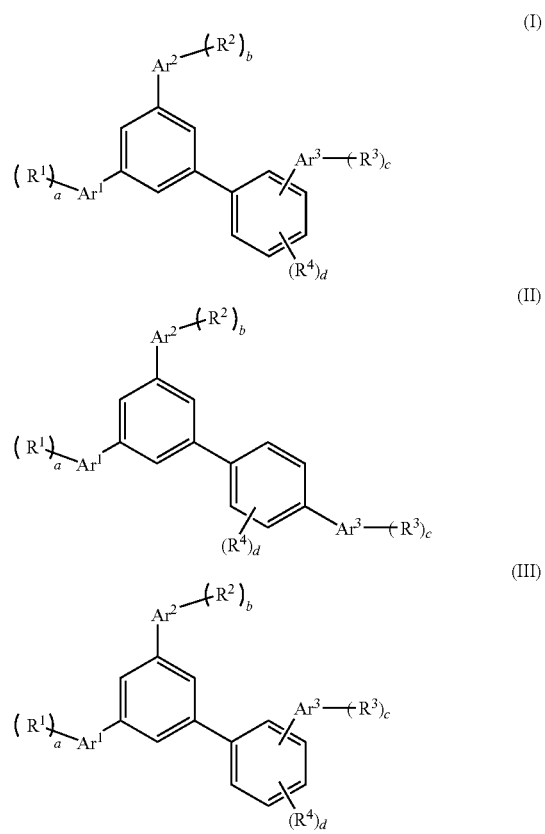

In the general formulae (I) to (III), $Ar^1$ and $Ar^2$ represent a substituted or unsubstituted condensed aromatic hydrocarbon group comprising 3 rings or more. However, when $Ar^1$ or $Ar^2$ represents an anthracene-9-yl group, 10th position of anthracene is not a hydrogen atom. Examples thereof include a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-chrysenyl group, a 2-chrysenyl group, a 6-chrysenyl group, a 1-naphthacenyl group, a 2-naphthacenyl group, a 9-naphthacenyl group, a 1-pyrenyl group, a 2-pyrenyl group, a 4-pyrenyl group, and the like. A 9-phenanthryl group, a 9-anthryl group, a 1-pyrenyl group, and the like are preferable.

In the general formulae (I) to (III), $Ar^3$ represents a substituted or unsubstituted phenyl group or a substituted or unsubstituted condensed aromatic hydrocarbon group comprising 2 rings or more. However, when $Ar^3$ represents an anthracene-9-yl group, 10th position of anthracene is not a hydrogen atom. Examples thereof include a phenyl group, a 1-naphtyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-chrysenyl group, a 2-chrysenyl group, a 6-chrysenyl group, a 1-naphthacenyl group, a 2-naphthacenyl group, a 9-naphthacenyl group, a 1-pyrenyl group, a 2-pyrenyl group, a 4-pyrenyl group, and the like.

A phenyl group, a 1-naphthyl group, a 2-naphtyl group, a 9-phenanthryl group, 9-anthryl group, 1-pyrenyl group, and the like are preferable.

The biphenyl derivatives of the present invention represents a condensed aromatic hydrocarbon group comprising $Ar^3$ having 2 rings or more in the above general formulae (I) to (III).

The biphenyl derivatives of the present invention represents a condensed hydrocarbon group comprising $Ar^3$ having 3 rings or more in the above general formulae (I) to (III).

The biphenyl derivatives of the present invention represent derivatives in which at least one of $Ar^1$ to $Ar^3$ in the above general formulae (I) to (III) represents a pyrenyl group.

In the above general formulae (I) to (III), the biphenyl derivatives of the present invention include an anthracene-9-yl group comprising a substituted or unsubstituted aromatic hydrocarbon group having ring carbon atoms of 6 to 50 at the 10th position thereof, and the substituent includes the similar groups to those illustrated in the following $R^1$ to $R^3$.

In the above general formulae (I) to (III), $R^1$ to $R^3$ each independently represents a substituted or unsubstituted aromatic hydrocarbon group having ring carbon atoms of 6 to 50, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having ring carbon atoms of 7 to 50, a substituted or unsubstituted aryloxy group having ring carbon atoms of 6 to 50, a substituted or unsubstituted arylthio group having ring carbon atoms of 6 to 50, a substituted or unsubstituted alkoxycarbonyl group having carbon atoms of 2 to 50, a silyl group which may be substituted with a substituted or unsubstituted alkyl group having carbon atoms of 1 to 50 or a substituted or unsubstituted aryl group having ring carbon atoms of 6 to 50, a carboxyl group, a halogen atom, a cyano group, a nitro group, or a hydroxy group.

In the general formulae (I) to (III), $R^4$ each independently represents, a substituted or unsubstituted aromatic hydrocarbon group having ring carbon atoms of 6 to 10, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having ring carbon atoms of 7 to 50, a substituted or unsubstituted aryloxy group having ring carbon atoms of 6 to 50, a substituted or unsubstituted arylthio group having ring carbon atoms of 6 to 50, a substituted or unsubstituted alkoxycarbonyl group having carbon atoms of 2 to 50, a silyl group which may be substituted with a substituted or unsubstituted alkyl group having carbon atoms of 1 to 50 or a substituted or unsubstituted aryl group having ring carbon atoms of 6 to 50, a carboxyl group, a halogen atom, a cyano group, a nitro group, or a hydroxy group.

Examples of the aromatic hydrocarbon group having ring carbon atoms of 6 to 50 represented by $R^1$ to $R^3$ in the general formulae (I) to (III) include a phenyl group, a 1-naphtyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-chrysenyl group, a 2-chrysenyl group, a 6-chrysenyl group, a 1-naphtacenyl group, a 2-naphtacenyl group, a 9-naphtacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a 4-phenylnaphthalene-1-yl group, a 6-phenylnaphthalene-2-yl group, a 4-(naphthalene-2-yl)phenyl group, a 3-(naphthalene-2-yl)phenyl group, a 2-(naphthalene-2-yl)phenyl group, a 4-(naphthalene-1-yl)phenyl group, a 3-(naphthalene-1-yl)phenyl group, a 2-(naphthalene-1-yl)phenyl group, an o-tolyl group, a m-tolyl group, a p-tolyl group, a p-t-butylphenyl group, p-(2-phenylpropyl)phenyl group, a 3-methyl-2-naphtyl group, a 4-methyl-1-naphtyl, a 4-methyl-1-anthryl group, a 4'-methylbiphenylyl group, and a 4"-t-butyl-p-terphenyl-4-yl group.

Examples of the substituted or unsubstituted aromatic hydrocarbon group having ring carbon atoms of 6 to 10 represented by $R^4$ in the general formulae (I) to (III), include a phenyl group, a 1-naphtyl group, a 2-naphtyl group, an o-tolyl group, a m-tolyl group, a p-tolyl group and a p-t-butylphenyl group among the above aromatic hydrocarbon groups.

Examples of the substituted or unsubstituted aromatic heterocyclic group having 5 to 50 ring carbon atoms represented by $R^1$ to $R^4$ in the general formulae (I) to (III) include an 1-pyrrolyl group, a 2-pyrrolyl group, a 3-pyrrolyl group, a pyradinyl group, a 2-pyridinyl group, a 3-pyridinyl group, a 4-pyridinyl group, an 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, an 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, an 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxanyl group, a 5-quinoxanyl group, a 6-quinoxanyl group, a 1-carbazolyl group, a 2-carbazolyl group, a 3-carbazolyl group, a 4-carbazolyl group, a 9-carbazolyl group, an 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, an 1-acridinyl group, a 2-acridinyl group, a 3-acridinyl group, a 4-acridinyl group, a 9-acridinyl group, an 1,7-phenanthrolin-2-yl group, an 1,7-phenanthrolin-3-yl group, an 1,7-phenanthrolin-4-yl group, an 1,7-phenanthrolin-5-yl group, an 1,7-phenanthrolin-6-yl group, an 1,7-phenanthrolin-8-yl group, an 1,7-phenanthrolin-9-yl group, an 1,7-phenanthrolin-10-yl group, an 1,8-phenanthrolin-2-yl group, an 1,8-phenanthrolin-3-yl group, an 1,8-phenanthrolin-4-yl group, an 1,8-phenanthrolin-5-yl group, an 1,8-phenanthrolin-6-yl group, an 1,8-phenanthrolin-7-yl group, an 1,8-phenanthrolin-9-yl group, an 1,8-phenanthrolin-10-yl group, an 1,9-phenanthrolin-2-yl group, an 1,9-phenanthrolin-3-yl group, an 1,9-phenanthrolin-4-yl group, an 1,9-phenanthrolin-5-yl group, an 1,9-phenanthrolin-6-yl group, an 1,9-phenanthrolin-7-yl group, an 1,9-phenanthrolin-8-yl group, an 1,9-phenanthrolin-10-yl group, an 1,10-phenanthrolin-2-yl group, an 1,10-phenanthrolin-3-yl group, an 1,10-phenanthrolin-4-yl group, an 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, an 1-phenazinyl group, a 2-phenazinyl group, an 1-phenothiazinyl group, a 2-phenothiazinyl group, a 3-phenothiazinyl group, a 4-phenothiazinyl group, a 10-phenothiazinyl group, an 1-phenoxazinyl group, an 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group and a 4-t-butyl-3-indolyl group.

Examples of the substituted or unsubstituted alkyl group having 1 to 50 carbon atoms represented by $R^1$ to $R^4$ in the general formulae (I) to (III) include a methyl group, an ethyl group, propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, a 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, an 2,3-diiodo-t-butyl group, an 1,2,3-triiodopropyl group, an aminomethyl group, an 1-aminoethyl group, a 2-aminoethyl group, a 2-aminoisobutyl group, an 1,2-diaminoethyl group, an 1,3-diaminoisopropyl group, a 2,3-diamino-t-butyl group, an 1,2,3-triamino-propyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyano-propyl group, a nitromethyl group, an 1-nitroethyl group, a 2-nitroethyl group, a 2-nitroisobutyl group, an 1,2-dinitroethyl group, an 1,3-dinitroisopropyl group, an 2,3-dinitro-t-butyl group, an 1,2,3-trinitropropyl group, and the like.

Examples of the substituted or unsubstituted cycloalkyl group having 3 to 50 carbon atoms represented by $R^1$ to $R^4$ in the general formulae (I) to (III) include a cyclopropyl group, a cyclobutyl group, a cyclopentyl group, a cyclohexyl group, a 4-methylcyclohexyl group, an 1-adamanthyl group, a 2-adamanthyl group, an 1-norbornyl group, and a 2-norbornyl group.

The alkoxy group represented by $R^1$ to $R^4$ in the general formulae (I) to (III) is a group represented by —OY, and examples of Y include the similar ones to the above alkyl groups.

Examples of the substituted or unsubstituted aralkyl group having 7 to 50 carbon atoms represented by $R^1$ to $R^4$ in the general formulae (I) to (III) include a benzyl group, an 1-phenylethyl group, a 2-phenylethyl group, an 1-phenylisopropyl group, a 2-phenylisopropyl group, a phenyl-t-butyl group, an α-naphthylmethyl group, an 1-α-naphthylethyl group, a 2-α-naphthylethyl group, an 1-α-naphthylisopropyl group, a 2-α-naphthylisopropyl group, a β-naphthylmethyl group, an 1-β-naphthylethyl group, a 2-β-naphthylethyl group, an 1-β-naphthylisopropyl group, a 2-β-naphthylisopropyl group, an 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, an 1-hydroxy-2-phenylisopropyl group, and an 1-chloro-2-phenylisopropyl group.

The substituted or unsubstituted aryloxyl group having 6 to 50 ring carbon atoms represented by $R^1$ to $R^4$ is a group represented by —OY'. Examples of the group represented by Y' include a phenyl group, an 1-naphthyl group, a 2-naphthyl group, an 1-anthryl group, a 2-anthryl group, 9-anthryl group, an 1-phenanthryl group, a 2-phenanthryl group, a 3-phenanthryl group, a 4-phenanthryl group, a 9-phenanthryl group, an 1-naphthacenyl group, a 2-naphthacenyl group, a 9-naphthacenyl group, an 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, a 2-pyrrolyl group, a 3-pyrrolyl group, pyradinyl group, a 2-pyridinyl group, 3-pyridinyl group, a 4-pyridinyl group, a 2-indolyl group, a 3-indolyl group, a 4-indolyl group, a 5-indolyl group, a 6-indolyl group, a 7-indolyl group, an 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, an 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, an 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxanyl group, a 5-quinoxanyl group, a 6-quinoxanyl group, a 1-carbazolyl group, a 2-carbazolyl group, a 3-carbazolyl group, a 4-carbazolyl group, an 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, an 1-acridinyl group, a 2-acridinyl group, a 3-acridinyl group, a 4-acridinyl group, a 9-acridinyl group, an 1,7-phenanthrolin-2-yl group, an 1,7-phenanthrolin-3-yl group, an 1,7-phenanthrolin-4-yl group, an 1,7-phenanthrolin-5-yl group, an 1,7-phenanthrolin-6-yl group, an 1,7-phenanthrolin-8-yl group, an 1,7-phenanthrolin-9-yl group, an 1,7-phenanthrolin-10-yl group, an 1,8-phenanthrolin-2-yl group, an 1,8-phenanthrolin-3-yl group, an 1,8-phenanthrolin-4-yl group, an 1,8-phenanthrolin-5-yl group, an 1,8-phenanthrolin-6-yl group, an 1,8-phenanthrolin-7-yl group, 1,8-phenanthrolin-9-yl group, an 1,8-phenanthrolin-10-yl group, an 1,9-phenanthrolin-2-yl group, an 1,9-phenanthrolin-3-yl group, an 1,9-phenanthrolin-4-yl group, an 1,9-phenanthrolin-5-yl group, an 1,9-phenanthrolin-6-yl group, an 1,9-phenanthrolin-7-yl group, an 1,9-phenanthrolin-8-yl group, an 1,9-phenanthrolin-10-yl group, an 1,10-phenanthrolin-2-yl group, an 1,10-phenanthrolin-3-yl group, an 1,10-phenanthrolin-4-yl group, an 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, an 1-phenazinyl group, a 2-phenazinyl group, an 1-phenothiazinyl group, a 2-phenothiazinyl group, a 3-phenothiazinyl group, a 4-phenothiazinyl group, an 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

The substituted or unsubstituted arylthio group having 6 to 50 ring carbon atoms represented by $R^1$ to $R^4$ in the general formulae (I) to (III) is represented by —SY' and examples of Y' include the similar groups to Y' of the aforementioned aryloxy groups.

The substituted or unsubstituted alkoxycarbonyl group having 2 to 50 carbon atoms represented by $R^1$ to $R^4$ in the general formulae (I) to (III) is represented by —COOZ and examples of Z include the similar groups to aforementioned alkyl groups.

Examples of substituent for each group of $Ar^1$ to $Ar^3$ and $R^1$ to $R^4$ in the general formulae (I) to (III) include an alkyl group such as a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, an 1,2-dihydroxyethyl group, an 1,3-dihydroxy-isopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, a 1,2-dichloroethyl group, an 1,3-dichloroisopropyl group, a 2,3-dichloro-t-butyl group, an 1,2,3-trichloropropyl group, bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, an aminomethyl group, an 1-aminoethyl group, a 2-aminoethyl group, a 2-aminoisobutyl group, a 1,2-diaminoethyl group, an 1,3-diaminoisopropyl group, a 2,3-diamino-t-butyl group, an 1,2,3-triamino-propyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyano-propyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, a cyclopropyl group, a cyclobutyl group, a cyclopentyl group, cyclohexyl group, a 4-methylcyclohexyl group, an 1-adamanthyl group, a 2-adamanthyl group, an 1-norbornyl group, and a 2-norbornyl group; an alkoxy group having carbon atoms of 1 to 6 such an ethoxy group, a methoxy group, an i-propoxy group, a n-propoxy group, a s-butoxy group, a t-butoxy group, a pentoxy group, a hexyloxy group, a cyclopentoxy group and a cyclohexyloxy group; an aryl group having carbon atoms of 5 to 40; an amino group substituted by an aryl group having ring carbon atoms of 5 to 40; an ester group containing an aryl group having ring carbon atoms of 5 to 40; an ester group containing an alkyl group having ring carbon atoms of 1 to 6; a cyano group, a nitro group and a halogen atom.

Examples of the silyl group, which may be substituted by a substituted or unsubstituted alkyl group having 1 to 50 carbon atoms or a substituted or unsubstituted aryl group having carbon atoms of 6 to 50, represented by $R^1$ to $R^4$ in the general formulae (I) to (III) include a trimethylsilyl group, a triethylsilyl group, a t-butyldimethylsilyl group, a vinyldimethylsiliy group, a propyldimethylsiliy group, and a triphenylsilyl group.

A halogen atom of $R^1$ to $R^4$ in the general formulae (I) to (III) includes a fluorine atom, a chlorine atom, a bromine atom, and an iodine atom.

In the general formulae (I) to (III), a to d each independently represents an integer of 0 to 3.

Examples of the biphenyl derivatives represented by the general formula (I) to (III) include the following, but not limited thereto;

-continued
AN-1
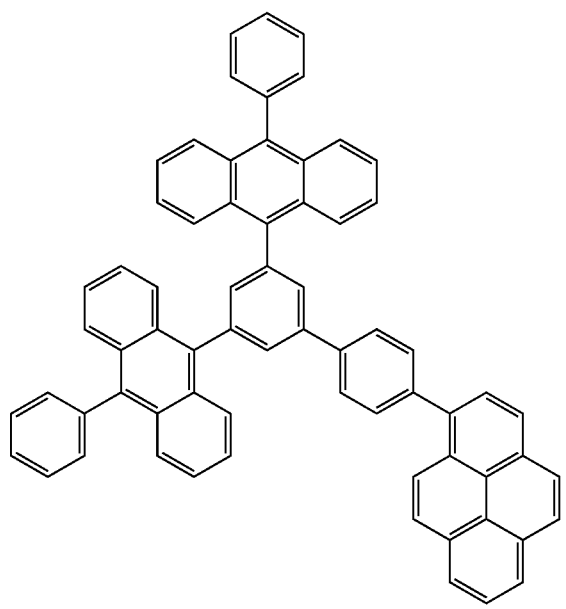
AN-4
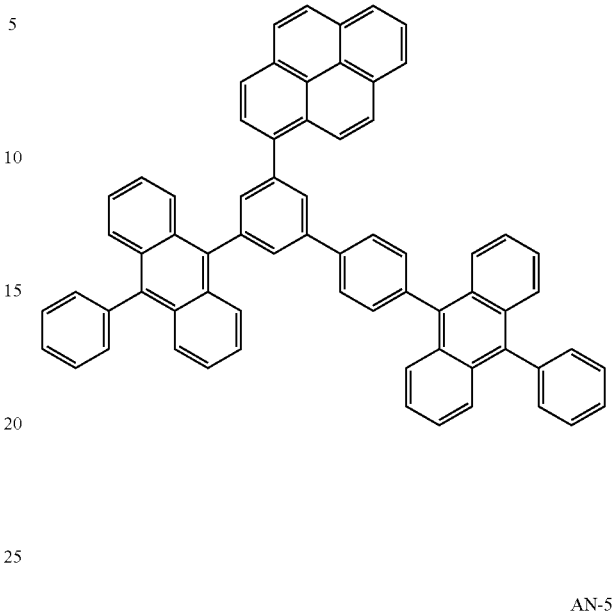
AN-2
AN-5
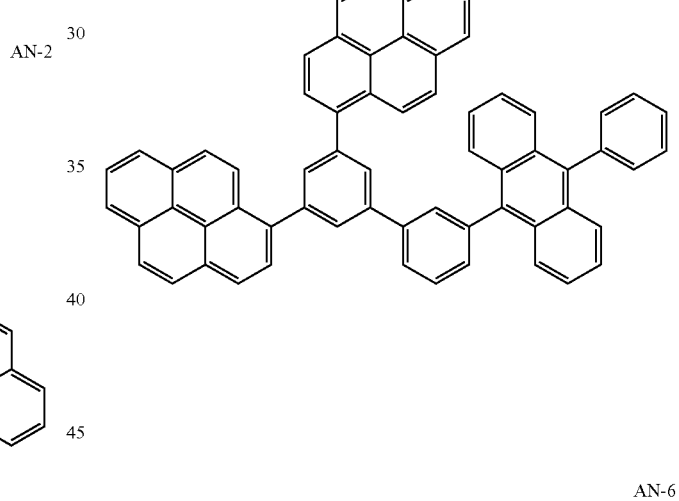
AN-3
AN-6
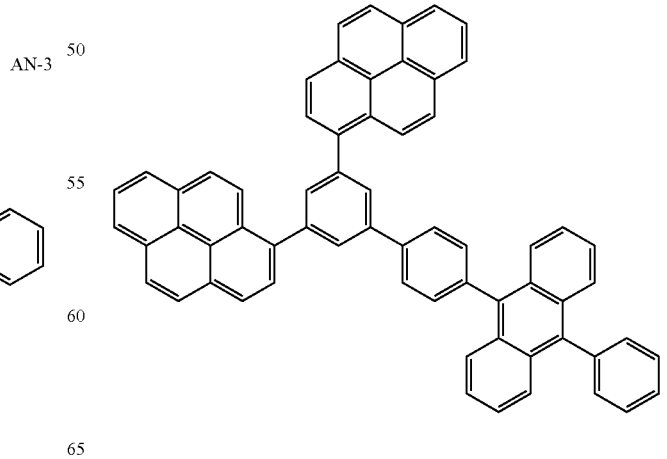

-continued
AN-7
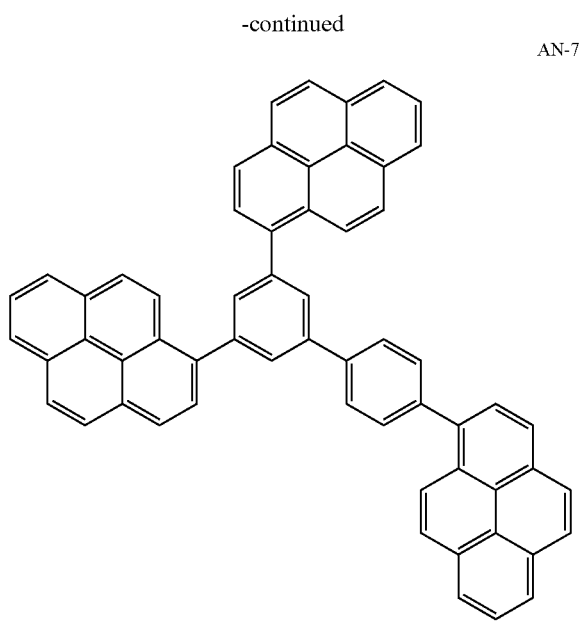
AN-8
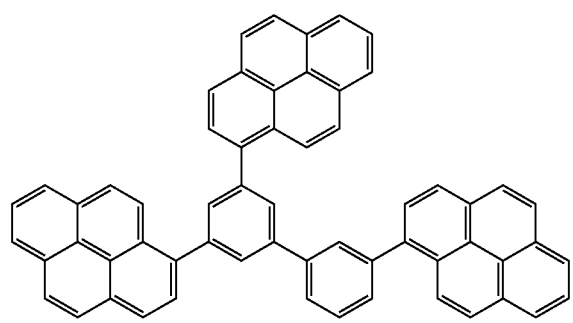
AN-9
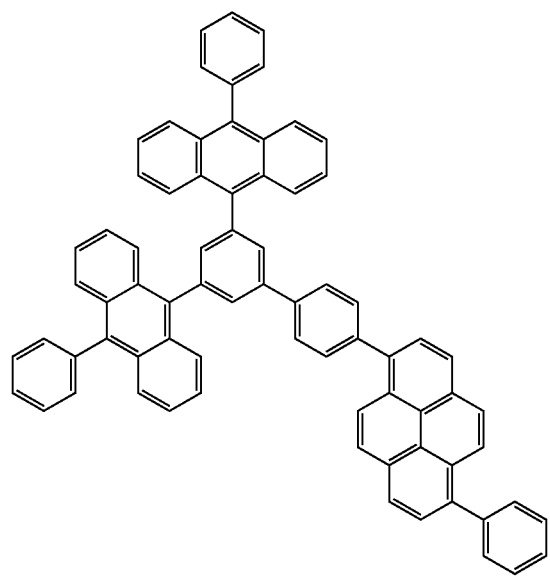
-continued
AN-10
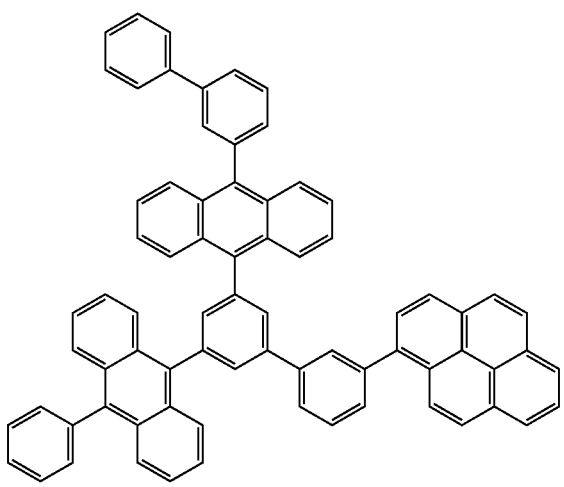
AN-11
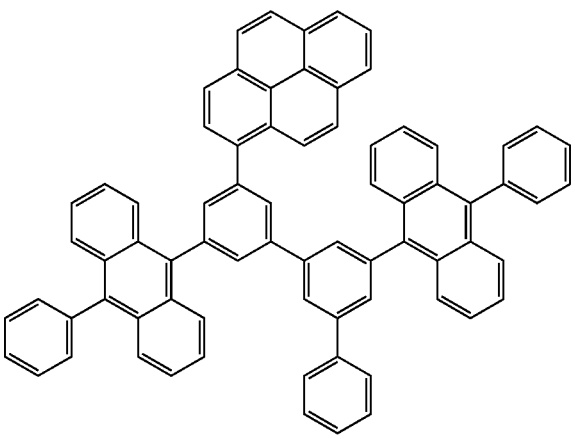
AN-12
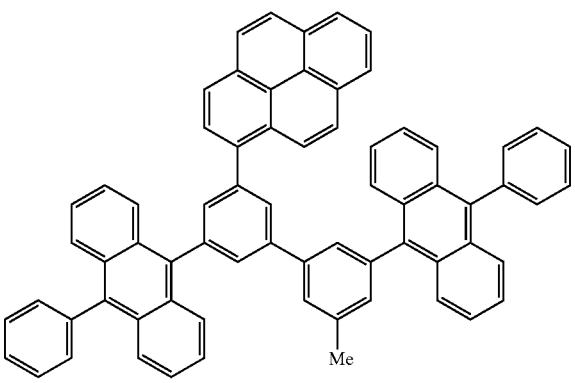

AN-13
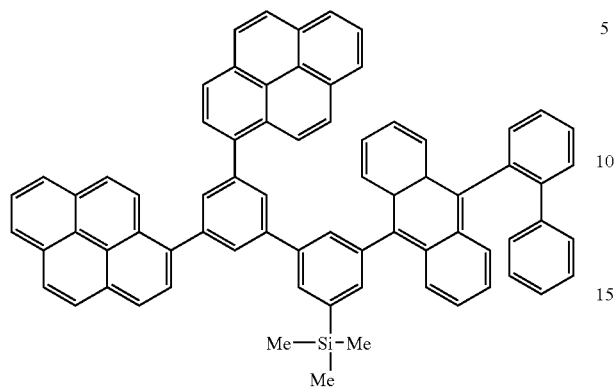
AN-14
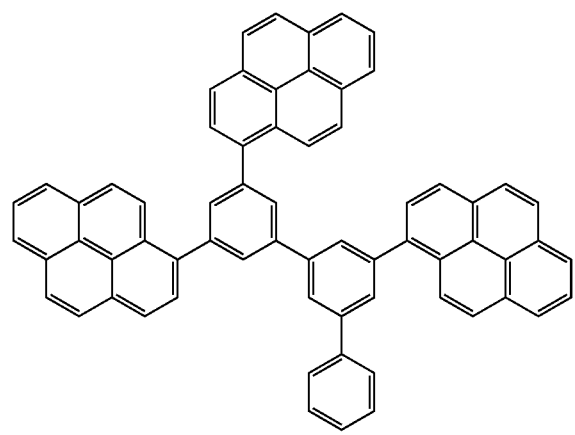
AN-15
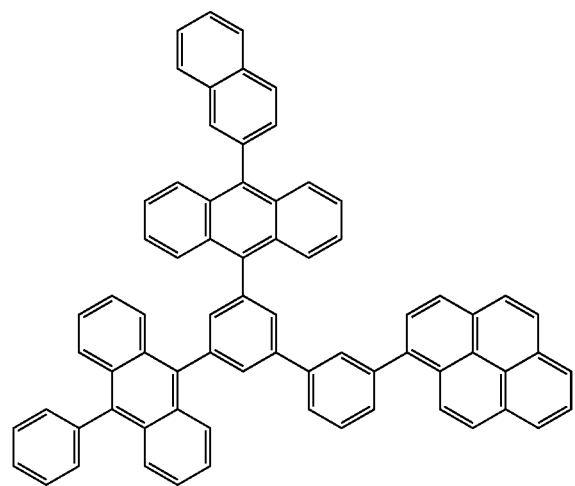
AN-16
AN-17
AN-18
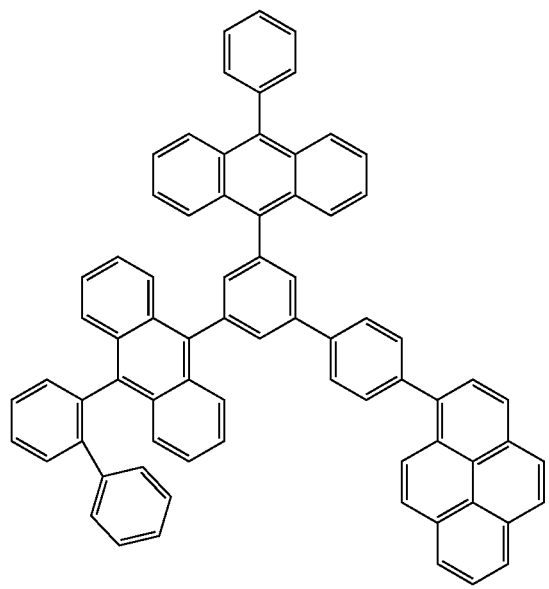

-continued
AN-19
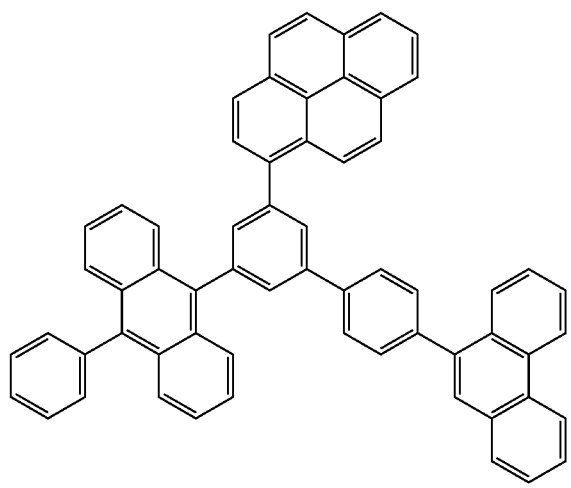
AN-21
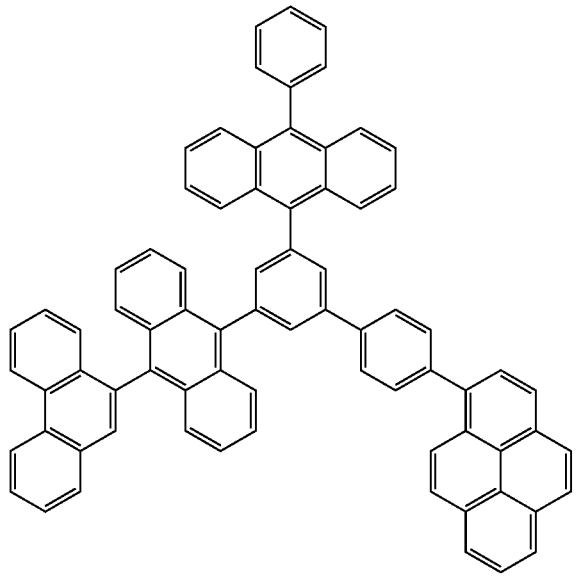
AN-20
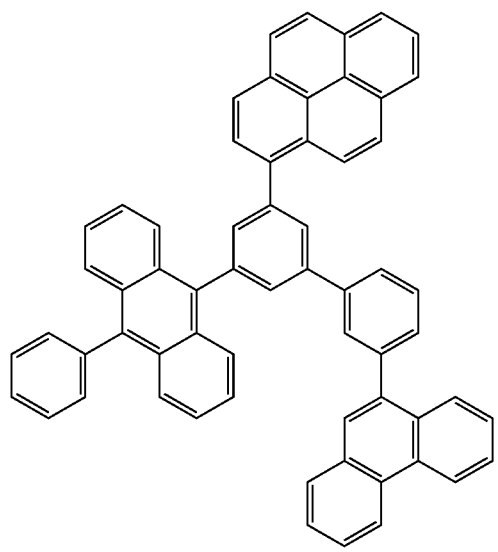
AN-22
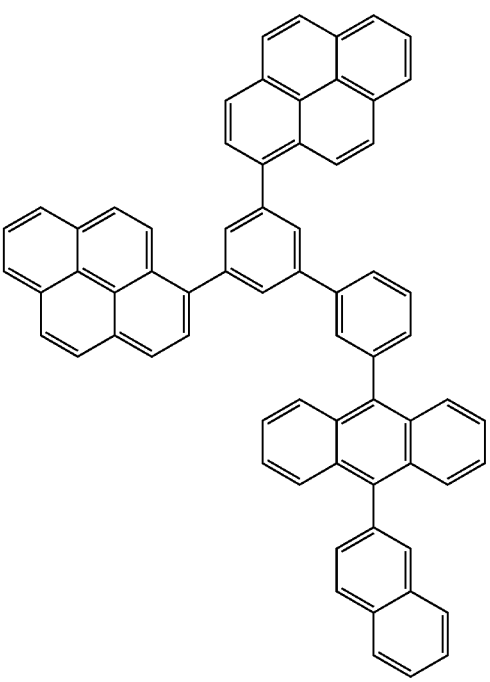

-continued
AN-23
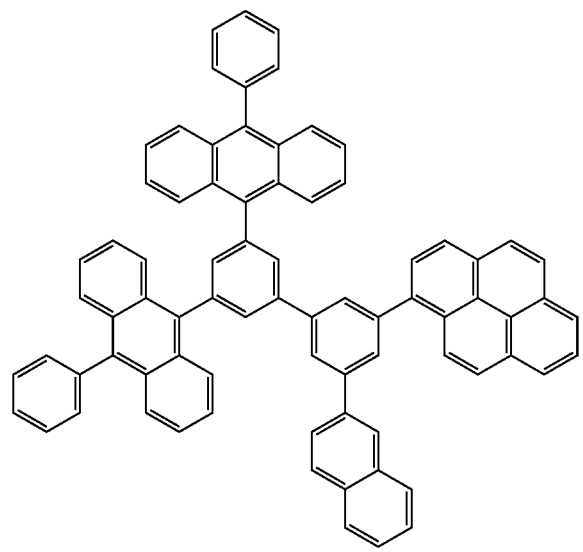
AN-24
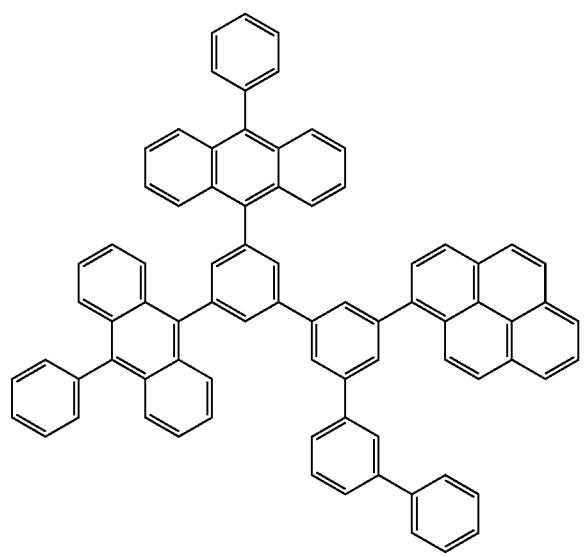
AN-25
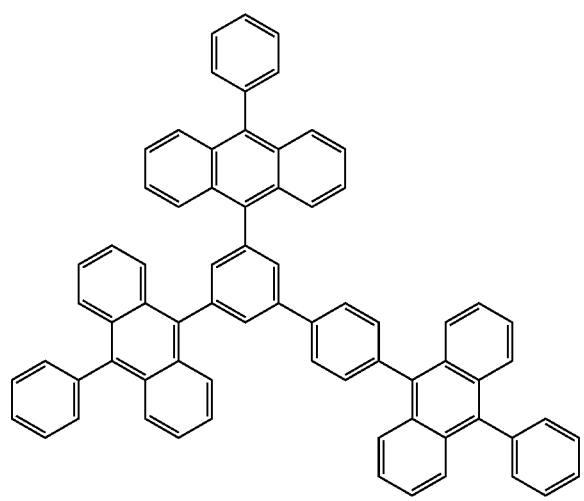
-continued
AN-26
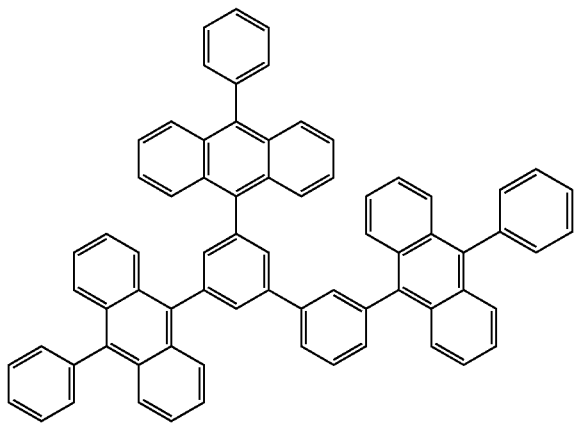
AN-27
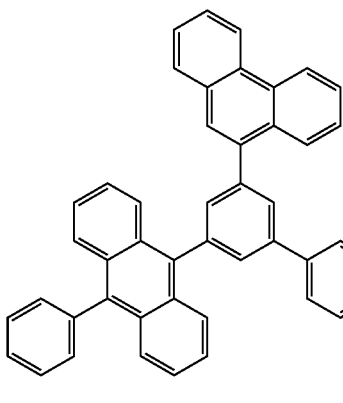
AN-28
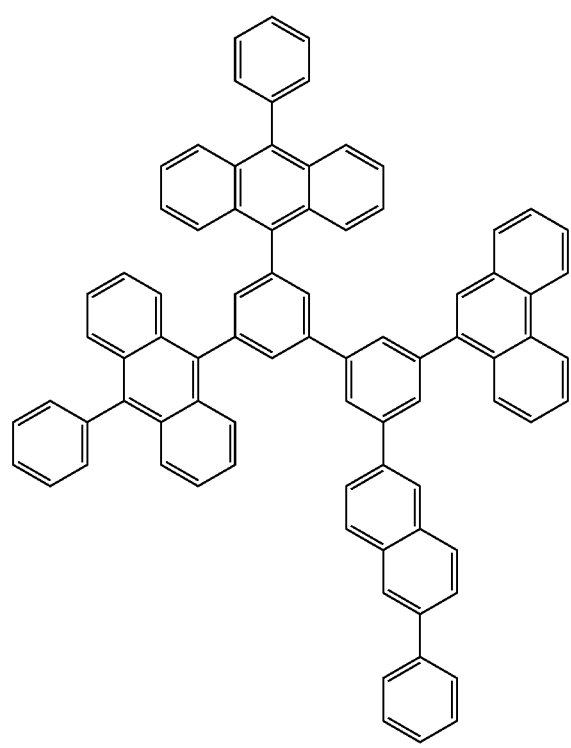

-continued
AN-29
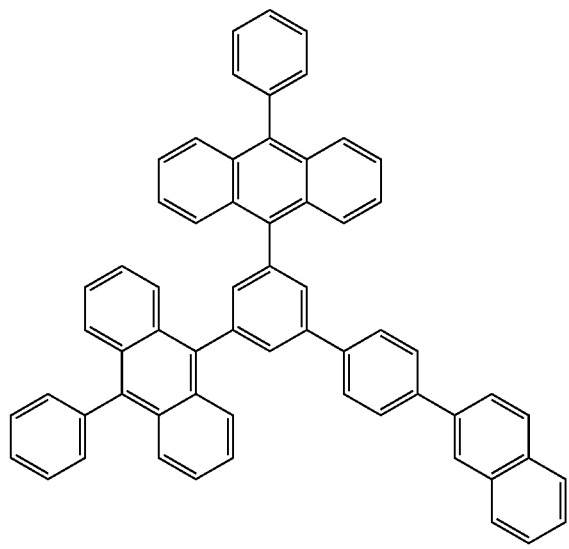
AN-30
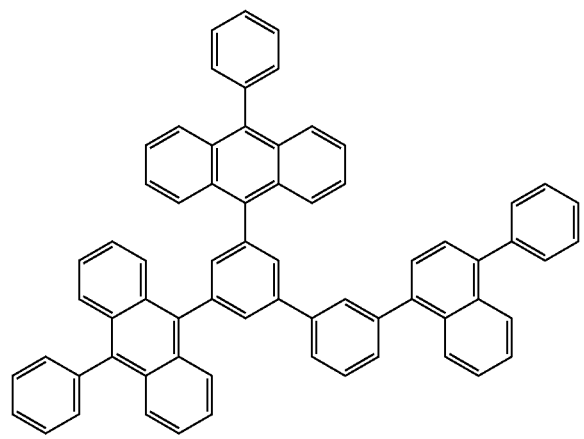
-continued
AN-31
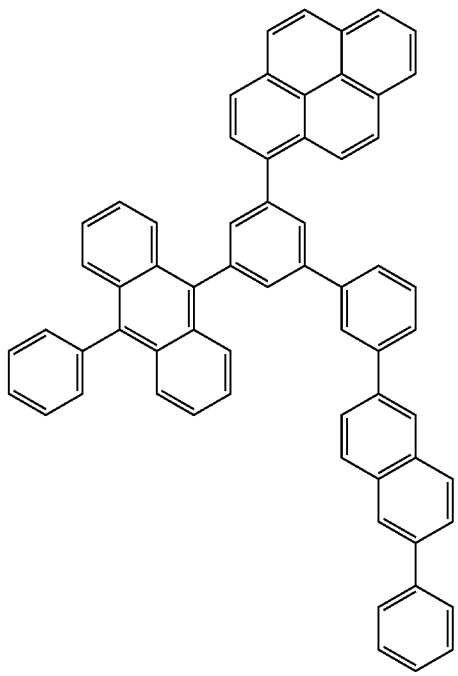
AN-32
AN-33

-continued
AN-34
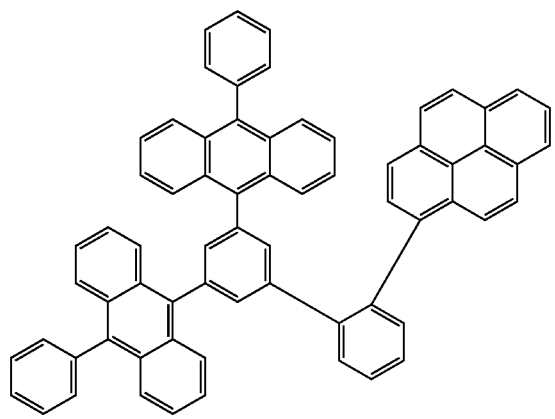
AN-35
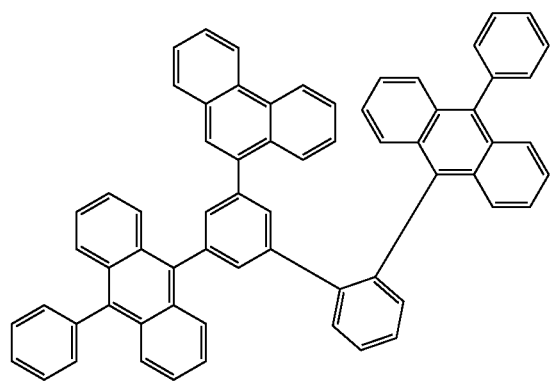
AN-36
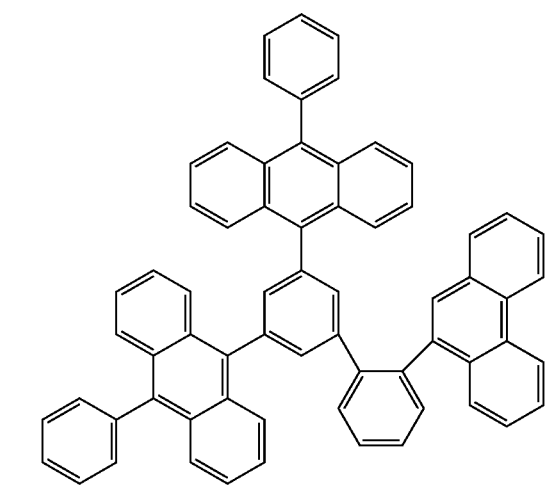
-continued
AN-37
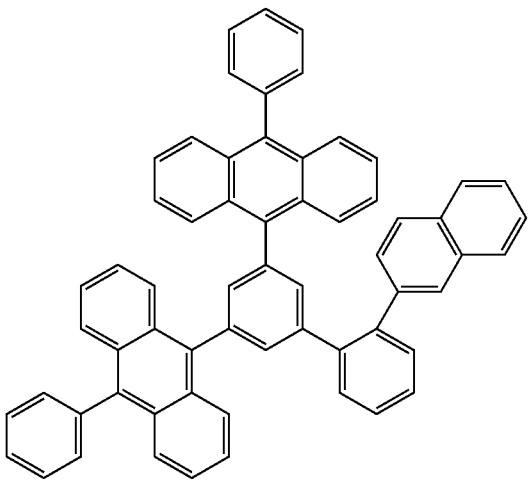
AN-38
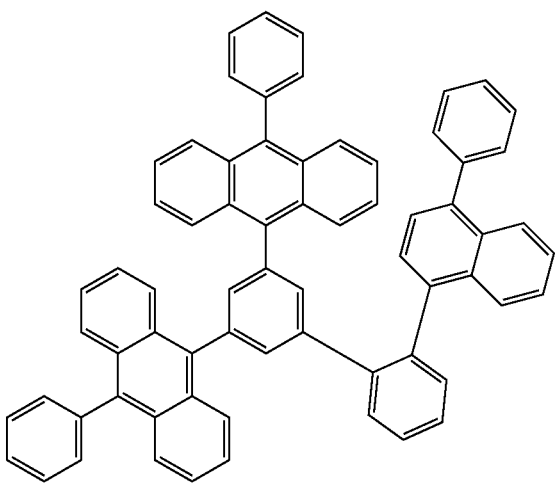
AN-39
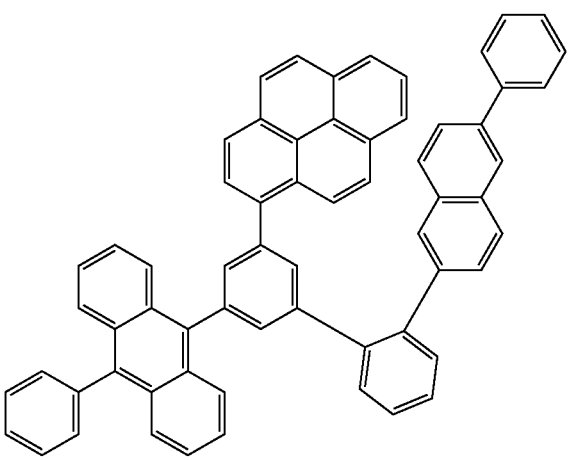

-continued
AN-40
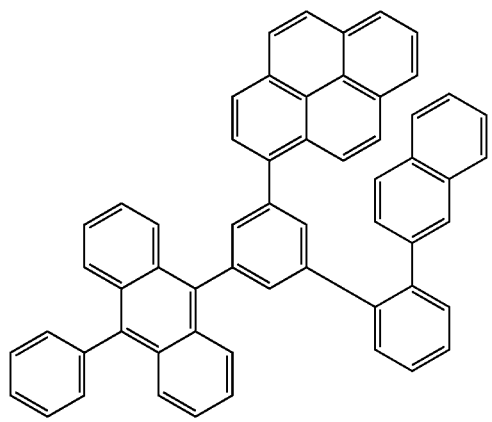
AN-41
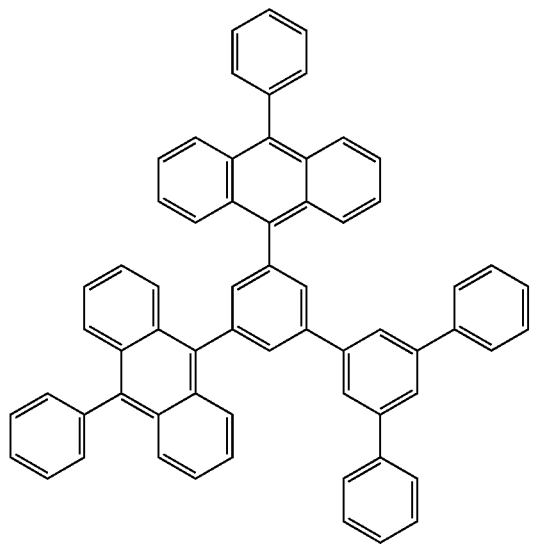
AN-42
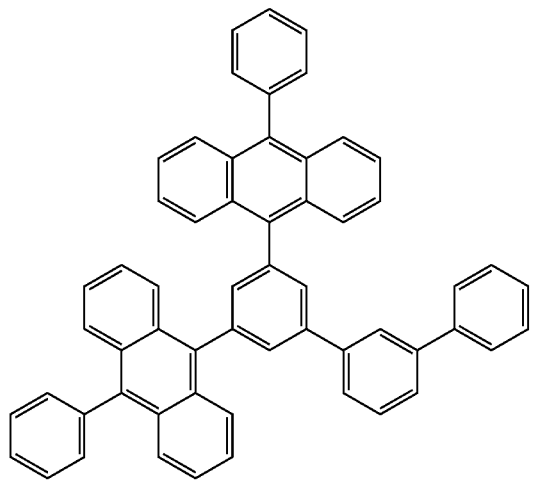
-continued
AN-43
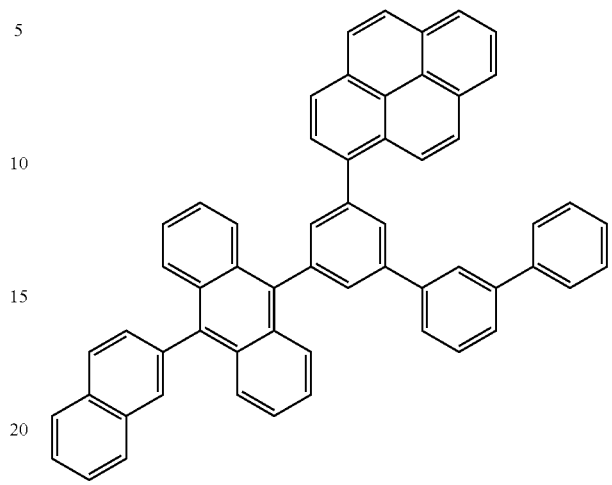
AN-44
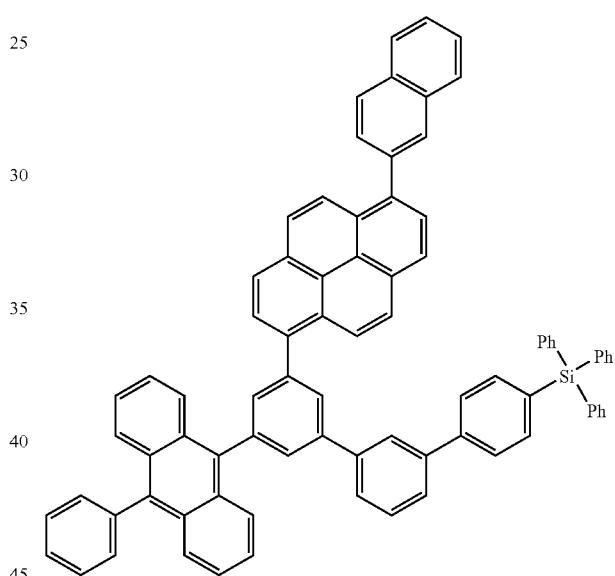
AN-45
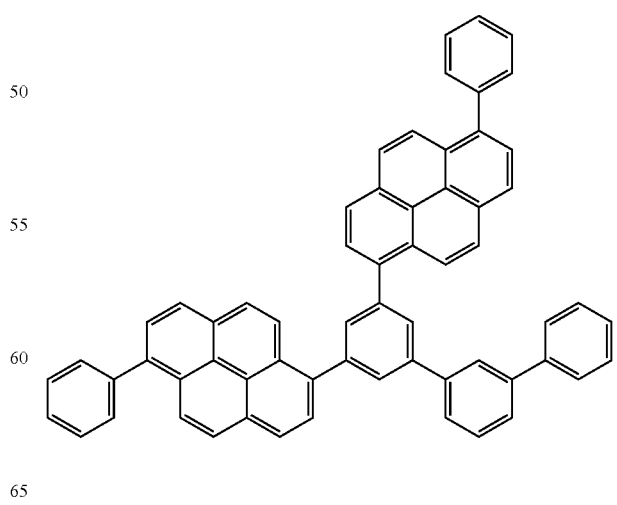

-continued

AN-46

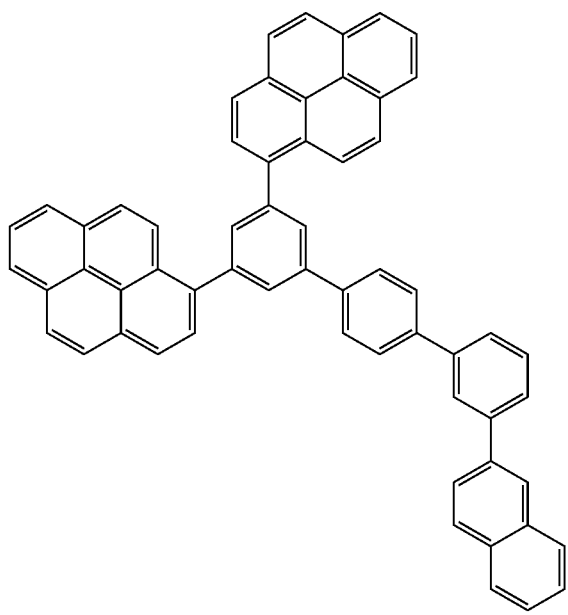

AN-47

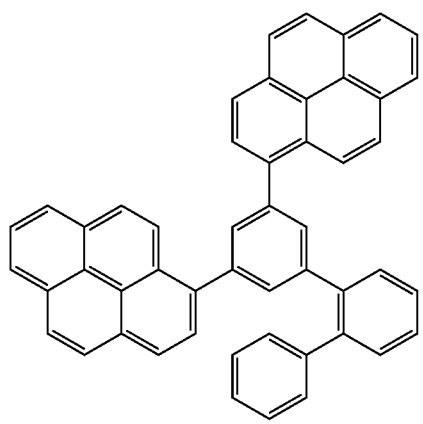

AN-48

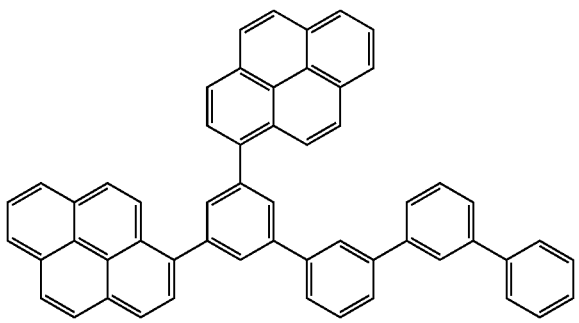

The biphenyl derivatives of the present invention are preferable for a material of an organic EL device, more preferable for a light emitting material thereof, and particularly preferable for a host material thereof.

The present invention provides an organic EL device which comprises at least one organic thin film layer sandwiched between a pair of electrode consisting of an anode and a cathode, wherein the organic thin film layer comprises at least a compound, singly or as a component of a mixture, selected from the biphenyl derivatives described in any one of the aforementioned general formulae (I) to (III).

Further, it is preferable that the aforementioned light emitting layer of the organic EL device of the present invention comprises an arylamine compound and/or a styrylamine compound additionally.

A compound represented by the following general formula (A) is preferable as the styrylamine compound:

(A)

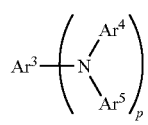

In the general formula (A), $Ar^3$ represents a group selected from a phenyl group, a biphenyl group, a terphenyl group, a stilbene group and a distyrylaryl group, $Ar^4$ and $Ar^5$ each represents a hydrogen atom, an aromatic hydrocarbon group having carbon atoms of 6 to 20, and $Ar^3$, $Ar^4$ and $Ar^5$ may have substituent. p represents an integer of 1 to 4. Further, it is preferable that $Ar^4$ and/or $Ar^5$ may be substituted by a styryl group.

Here, examples of the aromatic hydrocarbon group having carbon atoms of 6 to 20 include a phenyl group, a naphtyl group, an anthryl group, a phenanthryl group and a terphenyl group.

A compound represented by the following general formula (B) is preferable as the arylamine compound:

(B)

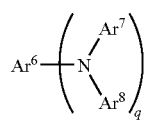

In the general formula (B), $Ar^6$ to $Ar^8$ each represents a substituted or unsubstituted aryl group having ring carbon atoms of 6 to 40. q represents an integer of 1 to 4.

Here, examples of the aryl group having ring carbon atoms of 6 to 40 include a phenyl group, a naphthyl group, an anthryl group, a phenanthryl group, a pyrenyl group, a coronyl group, a biphenyl group, a terphenyl group, a pyrrolyl group, a furanyl group, a thiophenyl group, a benzthiophenyl group, an oxadiazolyl group, a diphenylanthryl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzanthracenyl group, a phenylanthryl group, a bisanthracenyl group and an aryl group represented by the following general formulae (C) and (D). A naphtyl group, an anthryl group, a chrysenyl group, a pyrenyl group and an aryl group represented by the general formula (D) are preferable.

(C)

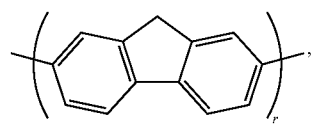

-continued

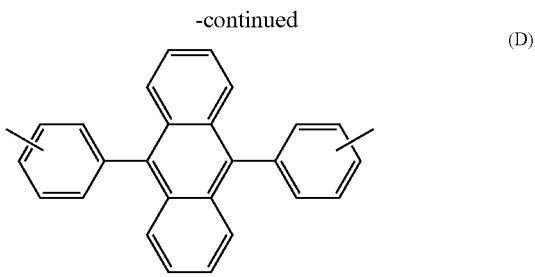

(D)

In the general formula (C), r represents an integer of 1 to 3.

In addition, a preferable substituent of the above aryl groups includes an alkyl group having carbon atoms of 1 to 6 such as an ethyl group, a methyl group, an i-propyl group, a n-propyl group, a s-butyl group, a t-butyl group, a pentyl group, a hexyl group, a cyclopentyl group, and a cyclhexyl group, an alkoxy group having carbon atoms of 1 to 6 such as an ethoxy group, a methoxy group, an i-propoxy group, a n-propoxy group, a s-butoxy group, a t-butoxy group, a pentoxy group, a hexyloxy group, a cyclopentoxy group, and a cyclohexyloxy group, an aryl group having ring carbon stoms of 5 to 40, an amino group substituted by an aryl group having ring carbon atoms of 5 to 40, an ester group comprising an aryl group having ring carbon atoms of 5 to 40, an ester group comprising an alkyl group having carbon atoms of 1 to 6, a cyano group, a nitro group, and a halogen group.

The following is a description of the construction of the organic EL device of the present invention.

Typical examples of the construction of the organic EL device of the present invention include:

(1) an anode/a light emitting layer/a cathode
(2) an anode/a hole injecting layer/a light emitting layer/a cathode;
(3) an anode/a light emitting layer/an electron injecting layer/a cathode;
(4) an anode/a hole injecting layer/a light emitting layer/an electron injecting layer/a cathode;
(5) an anode/an organic semiconductor layer/a light emitting layer/a cathode;
(6) an anode/an organic semiconductor layer/an electron blocking layer/a light emitting layer/a cathode;
(7) an anode/an organic semiconductor layer/a light emitting layer/an adhesion improving layer/a cathode;
(8) an anode/a hole injecting layer/a hole transporting layer/a light emitting layer/an electron injecting layer/a cathode;
(9) an anode/an insulating layer/a light emitting layer/an insulating layer/a cathode;
(10) an anode/an inorganic semiconductor layer/an insulating layer/a light emitting layer/an insulating layer/a cathode;
(11) an anode/an organic semiconductor layer/an insulating layer/a light emitting layer/an insulating layer/a cathode;
(12) an anode/an insulating layer/a hole injecting layer/a hole transporting layer/a light emitting layer/an insulating layer/a cathode; and
(13) an anode/an insulating layer/a hole injecting layer/a hole transporting layer/a light emitting layer/an electron injecting layer/a cathode.

Among those, the construction (8) is generally employed in particular; however, the construction of the organic EL device is not limited to those shown above as the examples.

In addition, in the organic EL device of the present invention, the biphenyl compounds of the present invention may be used for any one of the above layers, however, it is preferable that they are contained in a light emitting zone or a hole transporting zone among the above construction components. Further, it is particularly preferable that they are contained in a light emitting layer. The content thereof is selected in the range of from 30 to 100% by mole.

In general, the organic EL device is produced on a substrate which transmits light. It is preferable that the substrate which transmits light has a transmittance of light of 50% or greater in the visible region of wave length of 400 to 700 nm. It is also preferable that a flat and smooth substrate is employed.

As the substrate which transmits light, for example, glass sheet and synthetic resin sheet are advantageously employed. Specific examples of the glass sheet include soda-lime glass, glass containing barium and strontium, lead glass, aluminosilicate glass, borosilicate glass, barium borosilicate glass, quartz and the like. In addition, specific examples of the synthetic resin sheet include sheet made of polycarbonate resins, acrylic resins, polyethylene terephthalate resins, polyether sulfide resins, polysulfone resins and the like.

Next, the anode in the organic EL device of the present invention has a role of injecting holes into a hole transporting layer or a light emitting layer, and it is effective in having a work function of 4.5 eV or greater. Examples of the anode material include indium tin oxide (ITO), a mixture of indium oxide and zinc oxide (IZO), a mixture of ITO and cerium oxide (ITCO), a mixture of IZO and cerium oxide (IZCO), a mixture of indium oxide and cerium oxide (ICO), a mixture of zinc oxide and aluminum oxide (AZO), tin oxide (NESA), gold, silver, platinum and copper.

The anode can be prepared by forming a thin film of the electrode material described above in accordance with a process such as a vapor deposition process or a sputtering process.

When the light emitted from the light emitting layer is observed through the anode, it is preferable that the anode has a transmittance of the emitted light greater than 10%. It is also preferable that the sheet resistivity of the anode is several hundred Ω/□ or smaller. The thickness of the anode is, in general, selected in the range of from 10 nm to 1 µm and preferably in the range of from 10 to 200 nm depending on a kind of the material.

In the organic EL device of the present invention, the light emitting layer has the following functions:

(i) The injecting function: the function of injecting holes from the anode or the hole injecting layer and injecting electrons from the cathode or the electron injecting layer when an electric field is applied;
(ii) The transporting function: the function of transporting injected charges (electrons and holes) by the force of the electric field; and
(iii) The light emitting function: the function of providing the field for recombination of electrons and holes and leading the recombination to the emission of light.

As the process for forming the light emitting layer, a well known process such as the vapor deposition process, the spin coating process and the LB process may be employed. It is preferable that a light emitting layer is a molecular deposit film particularly. Here, the molecular deposit film is defined as a thin film formed by sedimentation from a gas phase material compound or a film formed by solidification from a material compound in a phase of solution or liquid. The molecular deposit film may be differentiated from a thin film formed by the LB process (a molecular accumulation film), based on the differences between agglomeration structures and higher-order structures, and also the differences resulting from functionalities thereof.

In addition, as shown in Japanese Patent Laid-open No. Shou 57(1982)-51781, to form a light emitting layer, a thin film may be formed in accordance with the spin coating and the like of the solution to be prepared by dissolving a binder such as resin and a material compound in solvent.

In the present invention, any well known light emitting materials may be optionally contained in the organic compound layer, and also a light emitting layer containing other well known light emitting materials may be laminated with the light emitting layer containing the light emitting materials of the present invention in an extent of not obstructing to achieve the objective of the present invention.

Next, the hole injecting/transporting layer is a layer which assists injection of holes into the light emitting layer and transport the holes to the light emitting zone. The layer exhibits a great mobility of holes and, in general, has an ionization energy as small as 5.5 eV or smaller. For the hole injecting/transporting layer, a material which transports holes to the light emitting layer at a small strength of the electric field is preferable. A material which exhibits, for example, a mobility of holes of at least $10^{-4}$ cm$^2$/V·sec under application of an electric field of from $10^4$ to $10^6$ V/cm is preferable.

As for a material to form the hole injecting/transporting layer, when it has the above preferable properties, any arbitrary material selected from conventional material, without any limitation, commonly used as a charge transporting material for the holes in photo conducting materials and well known material employed for the hole injecting layer in the EL device is usable. The aromatic amine derivatives include the compound represented by the following general formula:

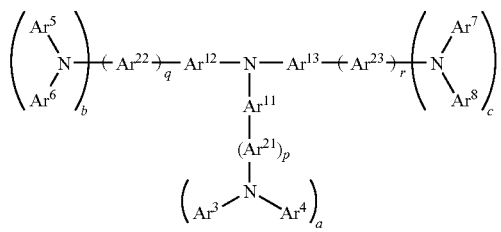

$Ar^{11}$ to $Ar^{13}$, $Ar^{21}$ to $Ar^{23}$ and $Ar^3$ to $Ar^8$ represent a substituted or unsubstituted aromatic hydrocarbon group having ring carbon atoms of 6 to 50 or an aromatic heterocyclic group having ring carbon atoms of 5 to 50. a to c and p to r each represents an integer of 0 to 3. $Ar^3$ and $Ar^4$, $Ar^5$ and $Ar^6$, and $Ar^7$ and $Ar^8$ may bond each other to form a saturated or unsaturated ring. Examples of the aromatic hydrocarbon group having ring carbon atoms of 6 to 50 include the similar groups to the aromatic hydrocarbon groups illustrated in $R^1$ to $R^3$ of the general formulae (I) to (III). Examples of the aromatic heterocyclic group having ring carbon atoms of 5 to 50 include the similar groups to the aromatic heterocyclic groups illustrated in $R^1$ to $R^4$ of the general formulae (I) to (III).

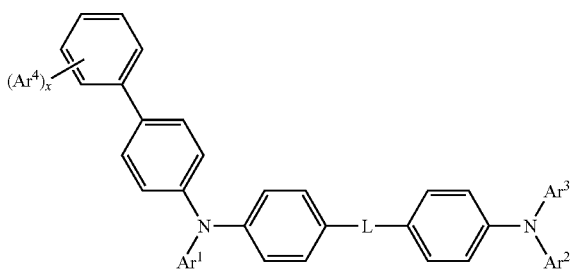

$Ar^1$ to $Ar^4$ each represents a substituted or unsubstituted aromatic hydrocarbon group having ring carbon atoms of 6 to 50 or an aromatic heterocyclic group having ring carbon atoms of 5 to 50. L represents a linking group: a single bond, a substituted or unsubstituted aromatic hydrocarbon group having ring carbon atoms of 6 to 50 or an aromatic heterocyclic group having ring carbon atoms of 5 to 50. x represents an integer of 0 to 5. $Ar^2$ and $Ar^3$ may bond each other to form a saturated or unsaturated ring. Examples of the aromatic hydrocarbon group having ring carbon atoms of 6 to 50 include the similar groups to the aromatic hydrocarbon groups illustrated in $R^1$ to $R^3$ of the general formulae (I) to (III). Examples of the aromatic heterocyclic group having ring carbon atoms of 5 to 50 include the similar groups to the aromatic heterocyclic groups illustrated in $R^1$ to $R^4$ of the general formulae (I) to (III).

Further examples include triazole derivatives (refer to U.S. Pat. No. 3,112,197, etc.), oxadiazole derivatives (refer to U.S. Pat. No. 3,189,447, etc.), imidazole derivatives (refer to Japanese Examined Patent KOKOKU No. Shou 37-16096, etc.), poly arylalkane derivatives (refer to U.S. Pat. Nos. 3,615,402, 3,820,989 and 3,542,544, Japanese Examined Patent KOKOKU Nos. Shou 45(1960)-555 and Shou 51(1966)-10983, Japanese Patent Application Laid-Open Nos. Shou 51(1966)-93224, Shou 55(1980)-17105, Shou 56(1981)-4148, Shou 55(1980)-108667, Shou 55(1980)-156953, Shou 56(1981)-36656, etc.), pyrazoline derivatives and pyrazolone derivatives (refer to U.S. Pat. Nos. 3,180,729 and 4,278,746, Japanese Application Patent Laid-Open Nos. Shou 55(1980)-88064, Shou 55(1980)-88065, Shou 49(1974)-105537, Shou 55(1980)-51086, Shou 56(1981)-80051, Shou 56(1981)-88141, Shou 57(1982)-45545, Shou 54(1979)-112637, Shou 55(1980)-74546, etc.), phenylenediamine derivatives (refer to U.S. Pat. No. 3,615,404, Japanese Examined Patent KOKOKU Nos. Shou 51-10105, Shou 46-3712 and Shou 47-25336, Japanese Unexamined Patent Application Laid-Open Nos. Shou 54-53435, Shou 54-110536, Shou 54-119925, etc.), arylamine derivatives (refer to U.S. Pat. Nos. 3,567,450, 3,180,703, 3,240,597, 3,658,520, 4,232,103, 4,175,961 and 4,012,376, Japanese Examined Patent KOKOKU Nos. Shou 49-35702 and Shou 39-27577, Japanese Unexamined Patent Application Laid-Open Nos. Shou 55-144250, Shou 56-119132 and Shou 56-22437, West German Patent No. 1,110,518, etc.), chalcone derivatives which is substituted with amino group (refer to U.S. Pat. No. 3,526, 501, etc.), oxazole derivatives (disclosed in U.S. Pat. No. 3,257,203, etc.), styryl anthracene derivatives (refer to Japanese Unexamine Patent Application Laid-Open No. Shou 56-46234, etc.), fluorenone derivatives (refer to Japanese Application Laid-Open No. Shou 54(1979)-110837, etc.), hydrazone derivatives (refer to U.S. Pat. No. 3,717,462, Japanese Patent. Application Laid-Open Nos. Shou 54(1979)-59143, Shou 55(1980)-52063, Shou 55(1980)-52064, Shou 55(1980)-46760, Shou 55(1980)-85495, Shou 57(1982)-11350, Shou 57(1982)-148749, Hei 2(1990)-311591, etc.), stilbene derivatives (refer to Japanese Patent Application Laid-Open Nos. Shou 61(1986)-210363, Shou 61(1986)-228451, Shou 61(1986)-14642, Shou 61(1986)-72255, Shou 62(1987)-47646, Shou 62(1987)-36674, Shou 62(1987)-10652, Shou 62-30255, Shou 60(1985)-93455, Shou 60(1985)-94462, Shou 60(1985)-174749, Shou 60(1985)-175052, etc.), silazane derivatives (U.S. Pat. No. 4,950,950), polysilane-based copolymers (Japanese Patent Application Laid-Open No. Hei 2(1990)-204996), aniline-based copolymers (Japanese Patent Application Laid-Open No. Hei 2(1990)-282263), an electroconductive polymer oligomer (particularly, thiophene oligomer) which is disclosed in Japanese Patent Application Laid-Open No. Hei 1(1989)-211399, etc.

With regard to the material of the hole injecting layer, the above materials are also employable, however, porphyrin compounds (disclosed in Japanese Patent Application Laid-Open No. Shou 63(1988)-295695, etc.), aromatic tertiary amine compounds and styryl amine compounds (refer to U.S. Pat. No. 4,127,412, Japanese Patent Application Laid-Open Nos. Shou 53(1978)-27033, Shou 54(1979)-58445, Shou 54(1979)-149634, Shou 54(1979)-64299, Shou 55(1980)-79450, Shou 55-144250, Shou 56(1981)-119132, Shou 61(1981)-295558, Shou 61(1981)-98353, Shou 63(1988)-295695, etc.) are preferable and the aromatic tertiary amine compounds are particularly preferable.

Further examples include, for example, 4,4'-bis(N-(1-naphthyl)-N-phenylamino)biphenyl (referred to as "NPD" hereinafter) having 2 condensed aromatic rings in its molecule described in U.S. Pat. No. 5,061,569, 4,4',4"-tris(N-(3-methylphenyl)-N-phenylamino)triphenyl amine (referred to as "MTDATA" hereinafter) made by connecting three triphenyl amine units to form a star burst type described in Japanese Patent Application Laid-Open No. Hei 4(1992)-308688, and the like.

In addition, the nitrogen-containing compounds represented by the following general formula, which were disclosed in Japanese Registered Patent No. 357197:

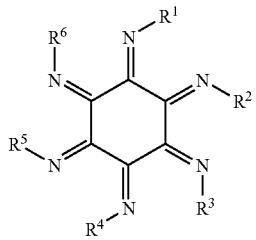

In the above general formula, $R^1$, $R^2$, $R^3$, $R^4$, $R^5$, and $R^6$ each represents a substituted or unsubstituted alkyl group, a substituted or unsubstituted aryl group, a substituted or unsubstituted aralkyl group, or a substituted or unsubstituted heterocyclic group. However, $R^1$, $R^2$, $R^3$, $R^4$, $R^5$, and $R^6$ may be the same with or different from each other. $R^1$ and $R^2$, $R^3$ and $R^4$, $R^5$ and $R^6$, or $R^1$ and $R^6$, $R^2$ and $R^3$, and $R^4$ and $R^5$ may bond to form condensed rings.

Further, the compounds represented by the following general formula disclosed in U.S Patent No. 2004-0113547 are also usable.

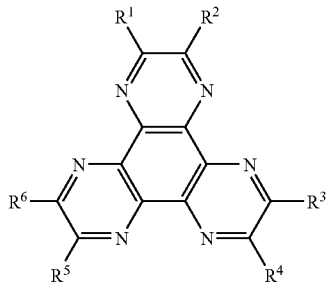

$R^1$ to $R^6$ each represents substituent, and preferably an electron accepting group such as a cyano group, a nitro group, a sulfonyl group, a carbonyl group, a trifluoromethyl group and halogen.

In addition, an inorganic compound such as p-type Si and p-type SiC may be used as a material for a hole injecting layer.

To form the hole injecting/transporting layer, a thin film may be formed from the above compounds in accordance with a well known process such as the vacuum vapor deposition process, the spin coating process, the casting process and the LB process. Although the thickness of the hole injecting/transporting layer is not particularly limited, the thickness is usually from 5 nm to 5 μm. When a hole transportation zone comprises a compound of the present invention, the hole injecting/transporting layer may be constructed by a layer consisting of at least one of the aforementioned materials, and also the hole injecting/transporting layer may be laminated by a hole injecting/transporting layer consisting of a compound different from them.

In addition, the organic semiconductor layer assists to inject the holes or to inject the electrons into the light emitting layer, and it is preferable for the organic semiconductor layer to have a electric conductivity of $10^{-10}$ S/cm or greater. With regard to a material for the organic semiconductor layer, electroconductive oligomer such as an oligomer having thiophene, an oligomer having arylamine disclosed in Japanese Laid-Open No. Hei 8(1996)-193191 and so on, electroconductive dendrimers such as a dendrimer having an arylamine and so on are employable.

The electron injection/transporting layer in the organic EL device of the present invention is a layer which assists injection of electrons into the light emitting layer and transports electrons to a light emitting zone, and it exhibits a great mobility of electrons. The adhesion improving layer is a layer which comprises a material having excellent adhesion to a cathode especially.

In addition, it has been known in organic EL devices that an interference between an emitted light just brought out from an anode and an emitted light brought out through reflection by the electrode has occurred due to the reflection by the electrode (the cathode in the present case). So as to utilize the interference effectively, an electron transporting layer is selected in the range of from several nm to several pm in film thickness. Further, when the film thickness is particularly thick, an electron mobility may be preferably at least $10^{-5}$ cm$^2$/V·sec under application of an electric field of from $10^4$ to $10^6$ V/cm in order to avoid increase of the voltage.

As the material for the electron injecting layer, 8-hydroxyquinoline, metal complexes of derivatives thereof and oxadiazole derivatives are preferable. Examples of the 8-hydroxyquinoline and metal complexes of derivatives thereof include metal chelates of oxinoid compounds including chelates of oxine (in general, 8-quinolinol or 8-hydroxyquinoline). For example, tris(8-quinolinolato)aluminum can be employed as the electron injecting material.

Further, examples of the oxadiazole derivatives include an electron transfer compound represented by the following general formula:

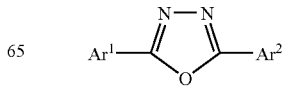

-continued

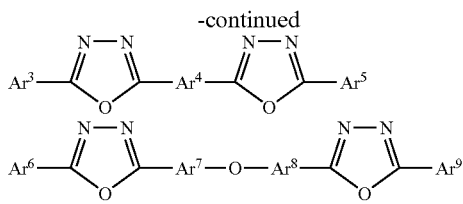

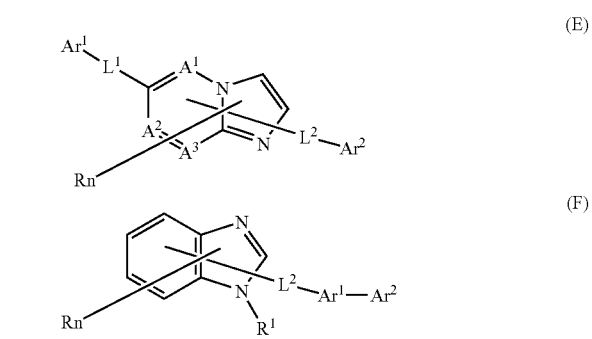

In the above general formula, $Ar^1$, $Ar^2$, $Ar^3$, $Ar^5$, $Ar^6$ and $Ar^9$ each independently represents a substituted or unsubstituted aryl group, which may be the same with or different from each other. Further, $Ar^4$, $Ar^7$ and $Ar^8$ each independently represents a substituted or unsubstituted arylene group, which may be the same with or different from each other.

Examples of the aryl group include a phenyl group, a biphenyl group, an anthryl group, a perilenyl group and a pyrenyl group. Further, examples of the arylene group include a phenylene group, a naphthylene group, a biphenylene group, an anthrylene group, a perilenylene group, the pyrenylene group and the like. Furthermore, examples of the substituent include an alkyl group having 1 to 10 carbon atoms, an alkoxy group having 1 to 10 carbon atoms, a cyano group and the like. With regard to the electron transfer compound, those compounds having a thin film forming capability are preferable.

Specific examples of the electron transfer compounds are shown below:

In the general formulae (E) and (F), $A^1$ to $A^3$ each independently represents a nitrogen atom or a carbon atom. $Ar^1$ represents a substituted or unsubstituted aryl group having ring carbon atoms of 6 to 60, or a substituted or unsubstituted heteroaryl group having ring carbon atoms of 3 to 60, $Ar^2$ represents a substituted or unsubstituted aryl group having ring carbon atoms of 6 to 60, a substituted or unsubstituted heteroaryl group having ring carbon atoms of 3 to 60, a substituted or unsubstituted alkyl group having ring carbon atoms of 1 to 20, or a substituted or unsubstituted alkoxy group having ring carbon atoms of 1 to 20, or a bivalent group thereof. However, any one of $Ar^1$ and $Ar^2$ represents a substi-

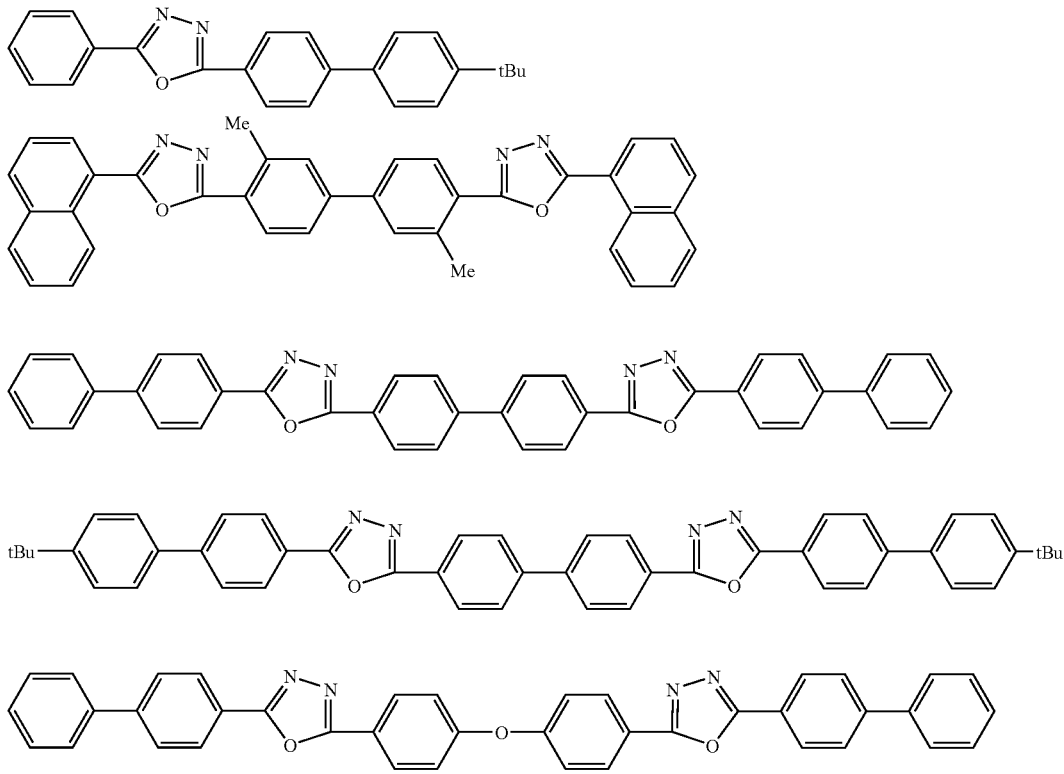

Further, as a material to be used for an electron injecting layer and an electron transporting layer, the nitrogen-containing heterocyclic derivatives represented by the following general formulae (E) to (J) may be also included.

tuted or unsubstituted condensed ring group having ring carbon atoms of 10 to 60, or a substituted or unsubstituted monohetero condensed ring group having ring carbon atoms of 3 to 60, or a bivalent group thereof.

$L^1$, $L^2$ and L each independently represents a single bond, a substituted or unsubstituted arylene group having ring carbon atoms of 6 to 60, a substituted or unsubstituted hetero arylene group having ring carbon atoms of 3 to 60, or a substituted or unsubstituted fluorenylene group.

R represents a hydrogen atom, a substituted or unsubstituted aryl group having ring carbon atoms of 6 to 60, a substituted or unsubstituted hetero aryl group having ring carbon atoms of 3 to 60, a substituted or unsubstituted alkyl group having carbon atoms of 1 to 20, or a substituted or unsubstituted alkoxy group having carbon atoms of 1 to 20. n represents an integer of 0 to 5, and when n is 2 or larger, a plural R may be the same with or different from each other. Further, neighboring Rs may bond each other to form a carbocyclic aliphatic ring or a carbocyclic aromatic ring.

$R^1$ represents a hydrogen atom, a substituted or unsubstituted aryl group having ring carbon atoms of 6 to 60, a substituted or unsubstituted hetero aryl group having ring carbon atoms of 3 to 60, a substituted or unsubstituted alkyl group having ring carbon atoms of 1 to 20, or a substituted or unsubstituted alkoxy group having ring carbon atoms of 1 to 20, or -L-$Ar^1$—$Ar^2$.

The nitrogen-containing heterocyclic derivatives represented by the general formula (G):

HAr-L-$Ar^1$—$Ar^2$ (G)

In the general formula (G), HAr represents a nitrogen-containing hetero ring having carbon atoms of 3 to 40, which may have substituent, L represents a single bond, an arylene group having ring carbon atoms of 6 to 60 which may have substituent, a heteroarylene group having ring carbon atoms of 3 to 60 which may have substituent, or a fluorenylene group which may have substituent. $Ar^1$ represents a bivalent aromatic hydrocarbon group having carbon atoms of 6 to 20 which may have substituent; $Ar^2$ represents an aryl group having carbon atoms of 6 to 60 which may have substituent, or a hetero aryl group having carbon atoms of 3 to 60 which may have substituent.

The silacyclopentadiene derivatives represented by the general formula (H):

In the general formula (H), X and Y each independently represents a saturated or unsaturated hydrocarbon group having carbon atoms of 1 to 6, an alkoxy group, an alkenyloxy group, an alkynyloxy group, a hydroxy group, a substituted or unsubstituted aryl group, a substituted or unsubstituted heterocyclic group, or a structure having a saturated or unsaturated ring formed by bonding X and Y. $R_1$ to $R_4$ each independently a hydrogen atom, a halogen atom, a substituted or unsubstituted alkyl group having carbon atoms of 1 to 6, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group, or a condensed structure of neighboring substituted or unsubstituted rings thereof.

The borane derivatives represented by the general formula (I):

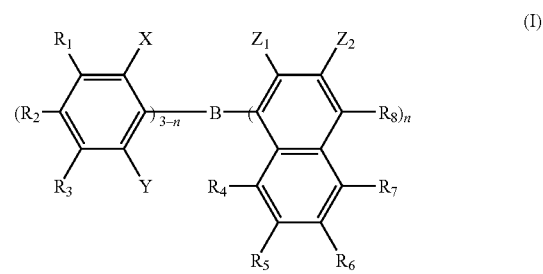

In the general formula (I), $R_1$ to $R_8$ and $Z_2$ each independently represents a hydrogen atom, a saturated or unsaturated hydrocarbon group, a heterocyclic group, a substituted amino group, a substituted boryl group, an alkoxy group or an aryloxy group; X, Y, and $Z_1$ each independently represents a saturated or unsaturated hydrocarbon group, an aromatic hydrocarbon group, a heterocyclic group, a substituted amino group, an alkoxy group or an aryloxy group; substituent of $Z_1$ and $Z_2$ may bond each other to form a condensed ring; n represents an integer of 1 to 3, $Z_{1S}$ may be different from each other when n is 2 or larger: however, excluding a case where n is 1, X, Y, and $R_2$ are methyl groups, and $R_8$ is a hydrogen atom or a substituted boryl group, and also a case where n is 3 and $Z_1$ is a methyl group.

In the general formula (J), $Q_1$ and $Q_2$ each independently represents a ligand represented by the following general formula (K), and L represents a ligand represented by a halogen atom, a substituted or unsubstituted alkyl group, a substituted or unsubstituted cycloalkyl group, a substituted or unsubstituted aryl group, a substituted or unsubstituted heterocyclic group, —$OR^1$, or —O—Ga-$Q^3(Q^4)$; wherein, $R^1$ represents hydrogen atom, a substituted or unsubstituted alkyl group, a substituted or unsubstituted cycloalkyl group, a substituted or unsubstituted aryl group, a substituted or unsubstituted heterocyclic group, and $Q^3$ and $Q^4$ are the same with $Q_1$ and $Q_2$.

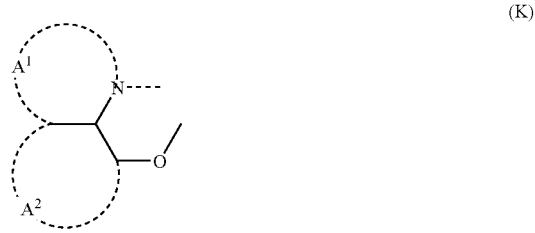

In the general formula (K), rings $A^1$ and $A^2$ each has 6 membered aryl ring structures which may have substituent.

The metal complexes have a strong property of a n-type semiconductor and a big capability of electron injection. In addition, due to low formation energy on forming the complexes, the affinity between the metals and ligands of the formed metal complexes is secured and fluorescence quantum efficiency for a light emitting material becomes larger.

Specific examples of substituent for rings $A^1$ and $A^2$, which form the ligand of the general formula (K), include a halogen atom such as chlorine, bromine, iodine and fluorine, a substituted or unsubstituted alkyl group such as a methyl group, an ethyl group, a propyl group, a butyl group, a s-butyl group, a t-butyl group, a pentyl group, a hexyl group, a heptyl group, an octyl group, a stearyl group, and a trichlorometyl group, a substituted or unsubstituted aryl group such as a phenyl group, a naphtyl group, a 3-methyphenyl group, a 3-methoxyphenyl group, a 3-fluorophenyl group, a 3-trichloromethyphenyl group, a 3-trifluoromethylphenyl group, and a 3-nitrophenyl group, a substituted or unsubstituted alkoxy group such as a methoxy group, a n-butoxy group, a t-butoxy group, a trichloromethoxy group, a trifluoroethoxy group, a pentafluoropropoxy group, 2,2,3,3-tetrafluoropropoxy group, 1,1,1,3,3,3-hexafluoro-2-propoxy group, and 6-(perfluoroethyl)hexyloxy group, a substituted or unsubstituted aryloxy group such as a phenoxy group, a p-nitrophenoxy group, a p-t-butylphenoxy group, a 3-fluorophenoxy group, a pentafluorophenyl group, and a 3-trifluoromethyphenoxy group, a substituted or unsubstituted alkylthio group such as a methylthio group, an ethylthio group, a t-butylthio group, a hexylthio group, an octylthio group, and a trifluoromethylthio group, a substituted or unsubstituted arylthio group such as a phenylthio group, a p-nitrophenylthio group, a p-t-butylphenylthio group, a 3-fluoohenylthio group, a pentafluorophenylthio, and 3-trifluoromethylphenylthio group, a cyano group, a nitro group, a mono- or di-substituted amino group such as an amino group, a methylamino group, a diethylamino group, an ethylamino group, a dipropylamino group, a dibutylamino group, and diphenylamino group, an acylamino group such as a bis(acetoxymethyl)amino group, a bis(acetoxyethyl)amino group, a bis(acetoxypropyl)amino group, and a bis(acetoxybutyl)amino group, a hydroxy group, a siloxy group, an acyl group, a carbamoyl group such as a methylcarbamoyl group, a dimethylcarbamoyl group, an ethylcarbamoyl group, a diethylcarbamoyl group, a propylcarbamoyl group, a butylcarbamoyl group, and a phenyl carbamoyl group, a carboxylic acid group, a sulfonic acid group, an imido group, a cycloalkyl group such as a cyclopentane group and a cyclohexyl group, an aryl group such as a phenyl group, a naphthyl group, a biphenyl group, an anthryl group, a phenanthryl group, a fluorenyl group, and a pyrenyl group, a heterocyclic group such as a pyridinyl group, a pyrazinyl group, a pyrimidinyl group, a pyridazinyl group, a triazinyl group, an indrynyl group, a quinolinyl group, an acridinyl group, a pyrrolidinyl group, a dioxanyl group, a piperidinyl group, a morpholizinyl, a piperazinyl group, a triatinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, and a planyl group. Further, the above substituents may bond each other to form a 6 member aryl ring or hetero ring additionally.

In the organic EL device of the present invention, it is preferable that a reductive dopant is added in either the electron transporting zone or an interfacial zone between the cathode and the organic layer. The reductive dopant used in the present invention is defined as a substance which reduces the electron transporting compound. Therefore, various compounds may be employed if they have a certain level of reduction capability. Examples of the preferable reductive dopant include at least one compound selected from the group comprising alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals and organic complexes of rare earth metals.

Examples of the preferable reductive dopant include at least one alkali metal selected from a group consisting of Na (the work function: 2.36 eV), K (the work function: 2.28 eV), Rb (the work function: 2.16 eV) and Cs (the work function: 1.95 eV) or at least one alkaline earth metal selected from a group consisting of Ca (the work function: 2.9 eV), Sr (the work function: 2.0 to 2.5 eV) and Ba (the work function: 2.52 eV); whose work function of 2.9 eV or less is particularly preferable. Among the above, the preferable reductive dopant include at least one alkali metal selected from a group consisting of K, Rb and Cs, the more preferred is Rb or Cs, and the most preferred is Cs. These alkali metals have particularly high capability of reduction so that improvement of an emission luminance and longer lasting of a lifetime of the organic EL device is realized. In addition, a combination of two or more of alkali metals is also preferable as a reductive dopant having 2.9 eV or less of the work function. In particular, a combination of Cs, for example with Na, K or Rb, or Na and K is preferable. By a combing and containing Cs therein, the reduction capability can be demonstrated effectively, and improvement of an emission luminance and longer lasting of a lifetime of the organic EL device is realized by adding it into an electron injecting area.

In the organic EL device of the present invention, an electron injecting layer formed with an insulating material or a semiconductor may be further interposed between the cathode and the organic thin film layer. The electron injecting layer effectively prevents leak of the electric current and improves the electron injecting capability. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenides since the electron injecting property can be improved. Preferable examples of the alkali metal chalcogenides include $Li_2O$, $K_2O$, $Na_2S$, $Na_2Se$ and $Na_2O$. Preferable examples of the alkaline earth metal chalcogenides include CaO, BaO, SrO, BeO, BaS and CaSe. In addition, preferable examples of the alkali metal halides include LiF, NaF, KF, CsF, LiCl, KCl, NaCl and the like. Further, preferable examples of the alkaline earth metal halides include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or as a component of a mixture. It is preferable that the inorganic compound constituting the electron transporting layer is in the form of crystallite or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

As the cathode for the organic EL device of the present invention, an electrode substance such as metal, alloy, electroconductive compound and those mixture having a small work function (4 eV or smaller) is employed. Examples of the electrode substance include sodium, sodium-potassium alloy, magnesium, lithium, cesium, magnesium-silver alloy, aluminum/aluminum oxide, $Al/Li_2O$, $Al/LiO$, $Al/LiF$, aluminum-lithium alloy, indium, rare earth metal and the like.

The cathode can be prepared by forming a thin film of the electrode material described above in accordance with a process such as the vapor deposition process and the sputtering process.

When the light emitted from the light emitting layer is observed through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of from 10 nm to 1 µm and preferably in the range of from 50 to 200 nm.

In general, an organic EL device tends to form defects in pixels due to leak and short circuit since an electric field is applied to ultra-thin films. To prevent the formation of the defects, a layer of an insulating thin film may be inserted between the pair of electrodes.

Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like. Mixtures and laminates of the above compounds can also be employed.

To produce an organic EL device of the present invention, for example, an anode, a light emitting layer and, where necessary, a hole injecting layer and an electron injecting layer are formed in accordance with the aforementioned process using the aforementioned materials, and the cathode is formed in the last step. An organic EL device may be produced by forming the aforementioned layers in the order reverse to that described above, i.e., a cathode being formed in the first step and an anode in the last step.

An embodiment of the process for producing an organic EL device having a construction in which an anode, a hole injecting layer, a light emitting layer, an electron injecting layer and a cathode are disposed sequentially on a light-transmitting substrate will be described in the following.

On a suitable light-transmitting substrate, a thin film made of a material for the anode is formed in accordance with the vapor deposition process or the sputtering process so that the thickness of the formed thin film is 1 µm or smaller and preferably in the range of 10 to 200 nm. The formed thin film is employed as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions in general are suitably selected in the following ranges: temperature of the deposition source: 50 to 450° C.; vacuum level: $10^{-7}$ to $10^{-3}$ Torr; deposition rate: 0.01 to 50 nm/second; temperature of the substrate: −50 to 300° C.; and film thickness: 5 nm to 5 µm; although the conditions of the vacuum vapor deposition are different depending on the employed compound (the material for the hole injecting layer) and the crystal structure and the recombination structure of the hole injecting layer to be formed.

Subsequently, the light emitting layer is formed on the hole injecting layer formed above. Also the formation of the light emitting layer can be made by forming the light emitting material according to the present invention into a thin film in accordance with the vacuum vapor deposition process, the sputtering process, the spin coating process or the casting process. The vacuum vapor deposition process is preferable because a uniform film can be easily obtained and the possibility of formation of pinholes is small. When the light emitting layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound. It is preferable that the thickness is in the range of from 10 to 40 nm.

Next, the electron-injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those for the hole injecting layer and the light emitting layer.

In the last step, the cathode is formed on the electron-injecting layer, and an organic EL device can be fabricated. The cathode is made of a metal and can be formed in accordance with the vacuum vapor deposition process or the sputtering process. It is preferable that the vacuum vapor deposition process is employed in order to prevent the lower organic layers from damages during the formation of the film.

In the above production of the organic EL device, it is preferable that the above layers from the cathode to the anode are formed successively while the production system is kept in a vacuum after being evacuated once.

The process for forming the layers in the organic EL device of the present invention is not particularly limited. A conventional process such as the vacuum vapor deposition process and the spin coating process can be used. The organic thin film layer comprising the compound represented by the aforementioned general formula (1) used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process.

The thickness of each layer in the organic thin film layer in the organic EL device of the present invention is not particularly limited, therefore, a thickness within the range of several nanometers to 1 µm is preferable so as to reduce the defects such as pin holes and improve the efficiency.

When a direct voltage is applied on the organic EL device produced in the above manner, when a direct voltage of 5 to 40 V is applied in the condition that the anode is connected to a positive electrode (+) and the cathode is connected to a negative electrode (−), then a light emission is observed. When the connection is reversed, no electric current is produced and no light is emitted at all. When an alternating voltage is applied on the organic EL device, the uniform light emission is observed only in the condition that the polarity of the anode is positive and the polarity of the cathode is negative. When an alternating voltage is applied on the organic EL device, any type of wave shape can be employed.

EXAMPLES

This invention will be described in further detail with reference to Examples, which do not limit the scope of this invention.

Synthesis Example 1

Synthesis of AN-4

Under the atmosphere of argon gas, 9 g of 1-(3,5-dibromophenyl)pyrene synthesized from 3,5-diboromoiodobenzene and 1-pyrenyl boronic acid was dissolved into 100 ml of anhydrous tetrahydrofuran (THF) and cooled down to −70° C. 14 ml of 1.6M n-butyllithium hexane solution was dropped therein and the resultant was stirred for 30 minutes. 5.9 g of 1,2-diiodoethane was added therein and the resultant was stirred for 5 hours. After the resultant was left overnight, water and methylene chloride were added therein, and then sodium bisulfite was added therein until the burned umber of the reaction solution was changed to yellow. The organic layer was extracted therefrom, and then it was washed by water and saturated salt water. Subsequently the organic layer was dried by using anhydrous sodium sulfate, and then the solvent was removed by distillation. The residue was refined through a silica gel chromatography (developing solvent: toluene/hexane=1/3) and then 8.4 g of 1-(3-bromo-4-iodophenyl)pyrene of cream color solid was obtained (Yield: 84%).

Under the atmosphere of argon gas, 8.2 g of obtained 1-(3-bromo-4-iodophenyl)pyrene, 3.4 g of 4-bromophenyl boronic acid, and 0.4 g of tetrakis(triphenylphophine)palladium were dissolved in 100 ml of toluene, and then 25 ml of 2M sodium carbonate aqueous solution was added therein, followed by 7 hours reflux on heating. After standing to cool, the precipitated solid was separated through filtration, and then followed by washing with water, methanol and heated toluene, and 6.3 g of 1-(3,4'-dibromobiphenyl-5-yl)pyrene of pale yellow solid was obtained (Yield: 72%).

Under the atmosphere of argon gas, 5 g of obtained 1-(3, 4'-dibromobiphenyl-5-yl)pyrene, 6.4 g of 10-phenylanthracene -9-boronic acid obtained by a known method and 0.45 g of tetrakis(triphenylphophine)palladium were dissolved in 100 ml of 1,2-dimethoxyethane (referred to as "DME", hereinafter), and then 30 ml of 2M sodium carbonate aqueous solution was added therein, followed by 9.5 hours reflux on heating. After the resultant was left overnight, the precipitated crystal was separated through filtration, and then followed by washing with water, methanol and heated toluene, and 5.2 g of the objective compound (AN-4) as the pale yellow solid was obtained (Yield: 62%). By Field Desorption Mass Spectrometry (FD-MS) analysis of the obtained compound, m/z=858 in the case of $C_{68}H_{42}$=858 was obtained, therefore AN-4 was confirmed.

Synthesis Example 2

Synthesis of AN-5

Under the atmosphere of argon gas, 6 g of tribromobenzene available as a commercial reagent, 9.4 g of 1-pyrenyl boronic acid and 0.88 g of tetrakis(triphenylphophine)palladium were dissolved in 150 ml of toluene, and then the 57 ml of 2M sodium carbonate aqueous solution was added therein, followed by 7 hours reflux on heating. After standing to cool, the precipitated solid was separated through filtration, and then followed by washing with water and methanol, and drying. The obtained solid was refined through a silica gel chromatography (developing solvent: toluene/hexane=1/3) and then 4.1 g of 3,5-dipyrenylbromobenzene of pale yellow solid was obtained (Yield: 38%).

Under the atmosphere of argon gas, 3.9 g of obtained 3,5-dipyrenylbromobenzene, 2.9 g of 3-(9-phenylanthracene-10-yl)phenyl boronic acid obtained by a known method and 0.16 g of tetrakis(triphenylphophine)palladium were dissolved in 80 ml of DME, and then 10 ml of 2M sodium carbonate aqueous solution was added therein, followed by 8 hours reflux on heating. After the resultant was left overnight, the precipitated crystal was separated through filtration, and then followed by washing with water, methanol and heated toluene, and 3.5 g of the objective compound (AN-5) as pale yellow solid was obtained (Yield: 62%). By Field Desorption Mass Spectrometry (FD-MS) analysis of the obtained compound, m/z=806 in the case of $C_{64}H_{38}$=806 was obtained, therefore AN-5 was confirmed.

Synthesis Example 3

Synthesis of AN-8

Under the atmosphere of argon gas, 3.5 g of 3,3',5-tribromobiphenyl synthesized from 3,5-dibromoiodobenzene and 3-bromophenyl boronic acid, 7.3 g of 1-pyrenyl boronic acid available as a commercial reagent, and 150 ml of MDE were mixed. Subsequently, 0.52 g of tetrakis(triphenylphophine) palladium and 67 ml of 2M sodium carbonate aqueous solution were added therein, followed argon displacement. After it was refluxed for 8 hours, it was left overnight. The predipitated crystal was separated through filtration, and then followed by washing with water, methanol and heated toluene, and 4.7 g of pale yellow solid as the objective compound (AN-8) was obtained (Yield: 69%). By Field Desorption Mass Spectrometry (FD-MS) analysis of the obtained compound, m/z=754 in the case of $C_{60}H_{34}$=754 was obtained, therefore AN-8 was confirmed.

Synthesis Example 4

Synthesis of AN-26

The objective compound (AN-26) of pale yellow solid was obtained similarly as Synthesis Example 3 except that 10-phenylanthracene-9-boronic acid was used in place of 1-pyrenyl boronic acid (Yield: 72%). By Field Desorption Mass Spectrometry (FD-MS) analysis of the obtained compound, m/z=910 in the case of $C_{72}H_{46}$=910 was obtained, therefore AN-26 was confirmed.

Synthesis Example 5

Synthesis of AN-30

Under the atmosphere of argon gas, 4.5 g of 3-(1-phenylnaphthalene-4-yl)phenyl boronic acid obtained by a known method, 5 g of 3,5 dibromoiodobenzene and 0.48 g of tetrakis (triphenylphophine)palladium were dissolved in 100 ml of toluene, and then the 21 ml of 2M sodium carbonate aqueous solution was added therein, followed by 8 hours reflux on heating. After resultant was left overnight, the precipitated crystal was separated through filtration, and followed by washing with water and methanol. The crystal was refined through a silica gel chromatography (developing solvent: toluene/hexane=1/3) and then 4.2 g of 3,5-dibromo-3'-(1-phenylnaphthalene-4-yl)biphenyl of cream color solid was obtained (Yield: 59%).

Under the atmosphere of argon gas, 4 g of obtained 3,5-dibromo-3'-(1-phenylnaphthalene-4-yl)biphenyl, and 5.1 g of 10-phenylanthracene-9-boronic acid obtained by a known method were dispersed in 100 ml of DME, and then 0.5 g of tetrakis(triphenylphophine)palladium and 25 ml of 2M sodium carbonate aqueous solution were added therein, and followed by 10 hours reflux on heating. After the resultant was left overnight, the precipitated crystal was separated through filtration, and then followed by washing with water, methanol and heated toluene, and 3.7 g of the objective compound (AN-30) as pale yellow solid was obtained (Yield: 55%). By Field Desorption Mass Spectrometry (FD-MS) analysis of the obtained compound, m/z=860 in the case of $C_{68}H_{44}$=860 was obtained, therefore AN-30 was confirmed.

Synthesis Example 6

Synthesis of AN-43

Under the atmosphere of argon gas, 10 g of 1-(3-bromo-5-iodophenyl)pyrene obtained in Synthesis Example 1, 4.1 g of 3-biphenylboronic acid and 0.5 g of tetrakis(triphenylphophine)palladium were dissolved in 120 ml of toluene, and then the 31 ml of 2M sodium carbonate aqueous solution was added therein, and followed by 7 hours reflux on heating. After standing to cool, the precipitated solid was separated by filtration, and followed by washing with water, methanol, and heated toluene so as to obtained 5.3 g of 1-[1',1":3",1'''-(5'-bromo)terphenyl-3'-yl]pyrene was obtained as pale yellow solid (Yield: 50%).

Under the atmosphere of argon gas, 5 g of obtained 1-[1', 1":3",1'''-(5'-bromo)terphenyl-3'-yl]pyrene, and 3.8 g of 10-(naphtherene-2-yl)anthracene-9-boronic acid obtained by a known method, and 0.23 g of tetrakis(triphenylphophine) palladium were dissolved in 80 g of DME, and then 15 ml of 2M sodium carbonate aqueous solution was added therein, and followed by 9.5 hours reflux on heating. After the resultant was left overnight, the precipitated crystal was separated through filtration, and then followed by washing with water, methanol and heated toluene, and 4.1 g of pale yellow solid as the objective compound (AN-43) was obtained (Yield: 57%). By Field Desorption Mass Spectrometry (FD-MS) analysis of the obtained compound, m/z=732 in the case of $C_{58}H_{36}$=732 was obtained, therefore AN-43 was confirmed.

Synthesis Example 7

Synthesis of AN-42

Under the atmosphere of argon gas, 4.0 g of 3,5-dibromo-m-terphenyl synthesized from 3,5-dibromoiodobenzene and 3-biphenyl boronic acid, and 6.8 g of 10-phenylanthracene-9-boronic acid were dispersed in 130 ml of DME, and then 0.6 g of tetrakis(triphenylphophine)palladium and 35 ml of 2M sodium carbonate aqueous solution were added therein, and followed by 10 hours reflux on heating. After the resultant was left overnight, the precipitated crystal was separated through filtration, and then followed by washing with water, methanol and heated toluene, and 4.8 g of pale yellow solid as the objective compound (AN-42) was obtained (Yield: 63%). By Field Desorption Mass Spectrometry (FD-MS) analysis of the obtained compound, m/z=734 in the case of $C_{58}H_{38}$=734 was obtained, therefore AN-42 was confirmed.

Example 1

Evaluation of AN-4

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N-diphenyl-4-aminophenyl)-N,N'-diphenyl-4,4'-diamino-1,1'-biphenyl having a film thickness of 60 nm (referred to as "TPD232 film", hereinafter) was formed so that the formed film covered the transparent electrode. The TPD232 film worked as the hole injecting layer. Successively, a layer of N,N,N',N'-tetra(4-biphenyl)-diaminobiphenylene with a film thickness of 20 nm (referred to as "TBDB layer", hereinafter) was formed over the TPD232 film. The formed film worked as the hole transporting layer. Further, a film of AN-4 was deposited thereby forming a film having a thickness of 40 nm. At the same time, the following amine compound BD1 having a styryl group as light emitting molecule was deposited with a weight ratio of AN-4: BD1=40:2. The formed film worked as the light emitting layer. On the film formed above, a film of Alq having a thickness 10 nm was formed. The formed film worked as the electron injecting layer. Thereafter, Li (the source of lithium: manufactured by SAES GETTERS Company) as a reductive dopant and Alq were binary vapor deposited and an Alq:Li film (film thickness: 10 nm) was formed as the electron injecting layer (or the cathode). On the Alq:Li film, metallic aluminum was deposited to form a metal cathode and an organic El device was fabricated. The device was tested under an electricity application, a blue light emission with an emission luminance of 600 cd/m² was observed at a voltage of 6.7 V and a current density of 10 mA/cm². In addition, when the device was tested under an electricity application at an initial luminance of 1,000 cd/m², the half lifetime was measured and the result was shown in Table 1.

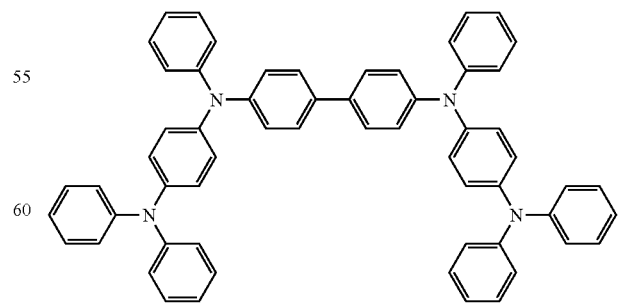

TPD234

-continued

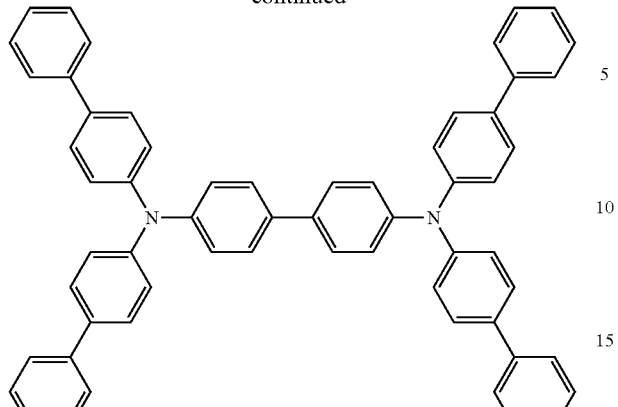

TBDB

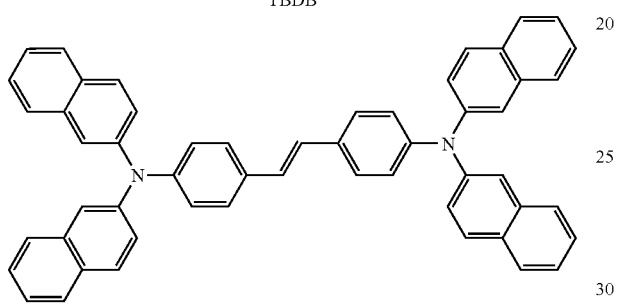

BD1

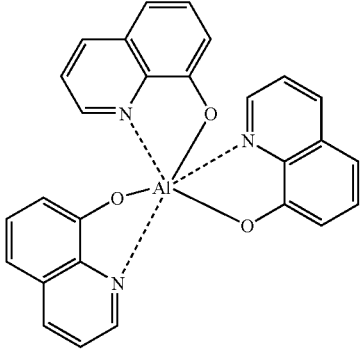

Alq

Examples 2 to 6

Organic EL devices were fabricated similarly as Example 1 except that the compounds in Table 1 in place of AN-4 were used as light emitting layer materials, respectively. In addition, when the devices were tested under an electricity application at an initial luminance of 1,000 cd/m², the half lifetimes were measured and the results were shown in Table 1.

Examples 7 and 8

Organic EL devices were fabricated similarly as Example 1 except that AN-42 or AN-4, and the following amine compound BD2 in place of the amine compound BD1 were used to form a light emitting layer. The half lifetimes thereof were measured similarly as Example 1. The results were shown in Table 1.

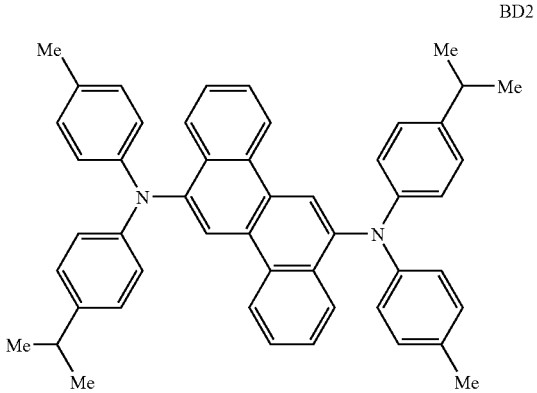

Example 9

An organic EL device was fabricated similarly as Example 1 except that the following amine compound BD3 in place of the amine compound BD1 was used to form a light emitting layer. The half lifetime thereof was measured similarly as Example 1. The result was shown in Table 1.

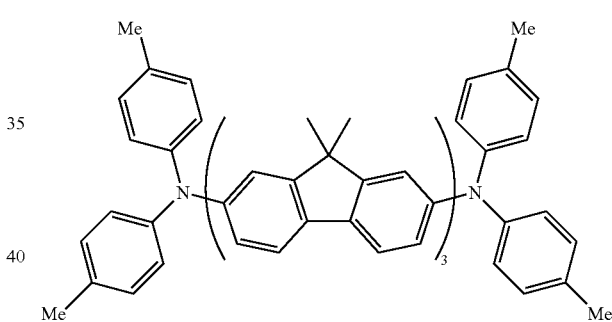

Comparative Examples 1 to 5

Organic EL devices were fabricated similarly as Example 1 except that the compounds in Table 1 in place of AN-4 were used to form light emitting layers. In addition, when the devices were tested under an electricity application at an initial luminance of 1,000 cd/m², the half lifetimes were measured and the results were shown in Table 1.

Comparative Examples 6 and 8

Organic devices were fabricated similarly as Example 1 except that an-5 in place of AN-4, and the amine compound BD2 or BD3 in place of BD-1 were used to form light emitting layers. In addition, when the devices were tested under an electricity application at an initial luminance of 1,000 cd/m², the half lifetimes were measured and shown in Table 1.

Comparative Example 8

An organic device was fabricated similarly as Example 1 except that an-6 in place of AN-4, and the amine compound DB2 in place of the amine compound BD1 were used to form a light emitting layer. In addition, when the device was tested under an electricity application at an initial luminance of 1,000 cd/m², the half lifetime was measured and the result was shown in Table 1.

The chemical structures of the compounds used in Comparative Examples are as follows;

TABLE 1

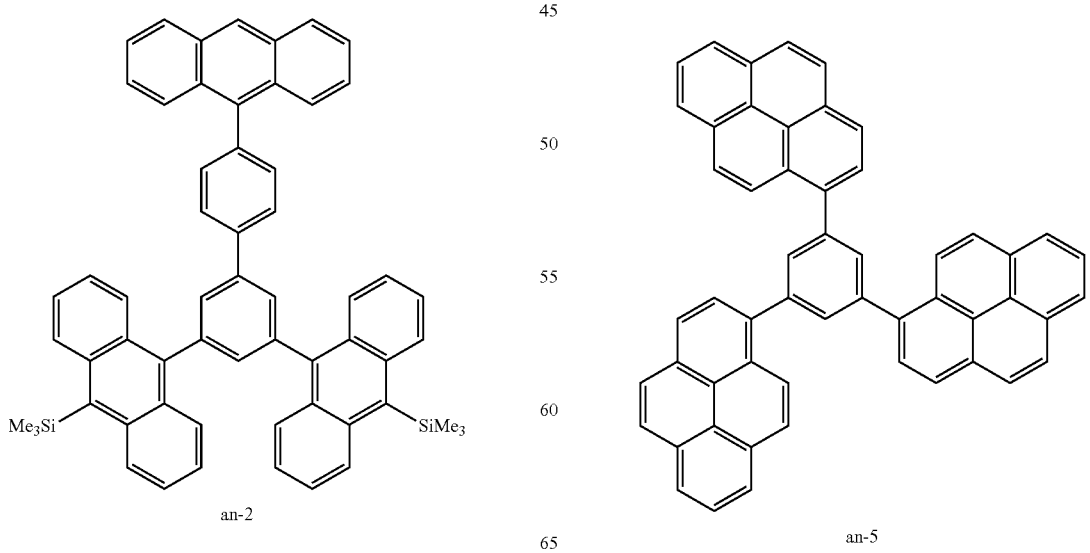

an-1 an-2

TABLE 1-continued

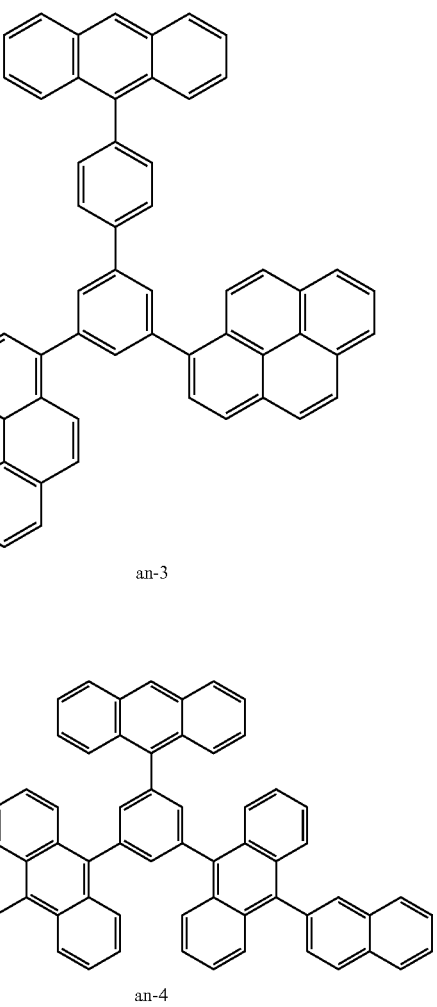

an-3 an-4 an-5

TABLE 1-continued

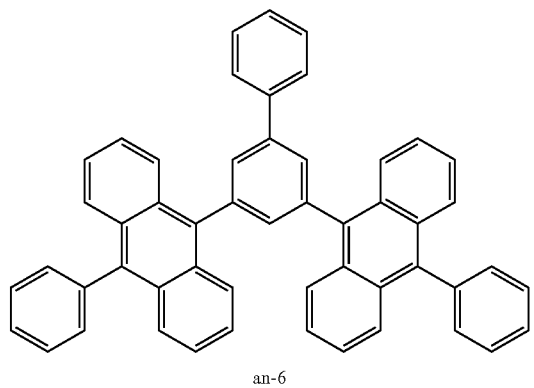

an-6

| | Compound for the light emitting layer | Half lifetime (Hours) |
|---|---|---|
| Example 1 | AN-4/BD1 | 4,100 |
| Example 2 | AN-5/BD1 | 4,000 |
| Example 3 | AN-8/BD1 | 3,200 |
| Example 4 | AN-26/BD1 | 3,800 |
| Example 5 | AN-30/BD1 | 3,500 |
| Example 6 | AN-43/BD1 | 3,400 |
| Example 7 | AN-42/BD2 | 3,500 |
| Example 8 | AN-4/BD2 | 3,600 |
| Example 9 | AN-4/BD3 | 3,000 |
| Comparative Example 1 | an-1/BD1 | 1,400 |
| Comparative Example 2 | an-2/BD1 | 800 |
| Comparative Example 3 | an-3/BD1 | 1,300 |
| Comparative Example 4 | an-4/BD1 | 1,800 |
| Comparative Example 5 | an-5/BD1 | 2,300 |
| Comparative Example 6 | an-5/BD2 | 2,000 |
| Comparative Example 7 | an-5/BD3 | 1,750 |
| Comparative Example 8 | an-6/BD2 | 2,100 |

Compared to the devices employing an-4 or an-5, the organic EL devices employing the biphenyl derivatives of the present invention have long lifetimes. In addition, when a biphenyl framework is contained therein, any one of the organic EL devices, which comprising the biphenyl derivatives of the present invention having aromatic hydrocarbon groups of 3 or more as substituent thereof, has a longer lifetime than those of the organic EL devices comprising an-6 having 2 aromatic hydrocarbon groups as substituent thereof. Further, an organic EL device has a long lifetime when an anthracene-9-yl group is substituent of the biphenyl framework and also an aromatic hydrocarbon group is bonded at 10th position of anthracene ring. Namely, the organic EL devices comprising AN-4, AN-5, AN-26, AN-30 and AN-43 have longer lifetimes than those of the organic EL devices comprising an-1 to an-4, each of which has a hydrogen atom at 10th position of anthracene ring.

INDUSTRIAL APPLICABILITY

As explained above in details, the organic EL device of the present invention comprising a biphenyl derivative of the present invention has a long lifetime. Therefore, the organic EL device has a high practical use, and it can be useful as a light source for applying it to a flat light emittor of a flat panel display for a television hanging on walls, a backlight for a display and the like. The biphenyl derivatives can be employed as a organic EL device, a hole injecting/transporting material, and also a charge transporting material for photosensitive material of electronic photograph and organic semiconductor.

What we claim is:

1. A biphenyl derivative represented by the following general formula (I):

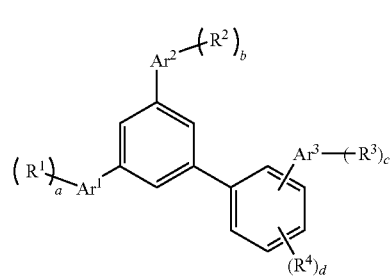

wherein, $Ar^1$ and $Ar^2$ represent a condensed aromatic hydrocarbon group comprising 3 rings or more, and $Ar^3$ represents an unsubstituted phenyl group or a condensed aromatic hydrocarbon group comprising 2 rings or more, wherein when any of $Ar^1$ to $Ar^3$ represents an anthracene-9-yl group, the 10th position of said anthracene-9-yl group is substituted with $R^1$ to $R^3$;

$R^1$ to $R^3$ each independently represents, a substituted or unsubstituted aromatic hydrocarbon group having ring carbon atoms of 6 to 50, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having ring carbon atoms of 7 to 50, a substituted or unsubstituted aryloxy group having ring carbon atoms of 6 to 50, a substituted or unsubstituted arylthio group having ring carbon atoms of 6 to 50, a substituted or unsubstituted alkoxycarbonyl group having carbon atoms of 2 to 50, a silyl group which may be substituted with a substituted or unsubstituted alkyl group having ring carbon atoms of 1 to 50 or a substituted or unsubstituted aryl group having ring carbon atoms of 6 to 50, a carboxyl group, a halogen atom, a cyano group, a nitro group, or a hydroxy group;

$R^4$ represents, a substituted or unsubstituted aromatic hydrocarbon group having ring carbon atoms of 6 to 10, a substituted or unsubstituted aromatic heterocyclic group having ring carbon atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having ring carbon atoms of 7 to 50, a substituted or unsubstituted aryloxy group having ring carbon atoms of 6 to 50, a substituted or unsubstituted arylthio group having ring carbon atoms of 6 to 50, a substituted or unsubstituted alkoxycarbonyl group having carbon atoms of 2 to 50, a silyl group which may be substituted with a substituted or unsubstituted alkyl group having ring carbon atoms of 1 to 50 or a substituted or unsubstituted aryl group having ring carbon atoms of 6 to 50, a carboxyl group, a halogen atom, a cyano group, a nitro group, or a hydroxy group; a to d each independently represents an integer for 0 to 3;

wherein when $Ar^3$ is an unsubstituted phenyl group and c represents an integer of 1 to 3, the substituted or unsubstituted aromatic hydrocarbon group represented by $R^3$ is selected from the group consisting of a phenyl group, a 1-naphtyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-chrysenyl group, a 2-chrysenyl group, a 6-chrysenyl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a 4-phenylnaphthalene-1-yl group, a 6-phenylnaphthalene-2-yl group, a 4-(naphthalene-2-yl)phenyl group, a 3-(naphthalene-2-yl)phenyl group, a 2-(naphthalene-2-yl)phenyl group, a 4-(naphthalene-1-yl)phenyl group, a 3-(naphthalene-1-yl)phenyl group, a 2-(naphthalene-1-yl)phenyl group, an o-tolyl group, a m-tolyl group, a p-tolyl group, a p-t-butyiphenyl group, p-(2-phenylpropyl)phenyl group, a 3-methyl-2-naphtyl group, a 4-methyl-1-naphtyl, a 4-methyl-1-anthryl group, a 4'-methylbiphenylyl group, and a 4"-t-butyl-p-terphenyl-4-yl group.

2. The biphenyl derivative according to claim 1 represented by the following general formula (II):

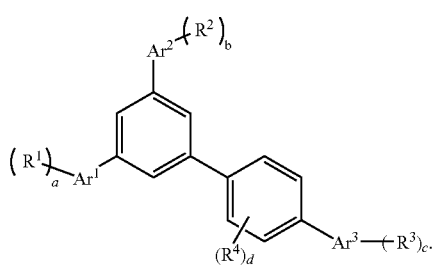

(II)

3. The biphenyl derivative according to claim 1 represented by the following general formula (III):

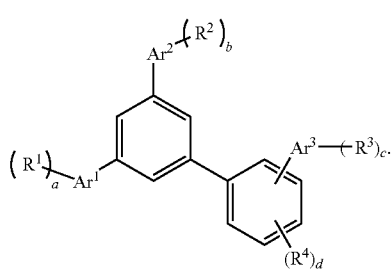

(III)

4. The biphenyl derivative according to any one of claims 1 to 3, wherein $Ar^3$ represents a condensed aromatic hydrocarbon group comprising 2 rings or more in the general formulae (I) to (III).

5. The biphenyl derivative according to any one of claims 1 to 3, wherein $Ar^3$ represents a condensed aromatic hydrocarbon group comprising 3 rings or more in the general formulae (I) to (III).

6. The biphenyl derivative according to any one of claims 1 to 3, wherein at least one of $Ar^1$ to $Ar^3$ represents a pyrenyl group in the general formulae (I) to (III).

7. The biphenyl derivative according to any one of claims 1 to 3, wherein at least one of $Ar^1$ to $Ar^3$ represents a substituted anthracene-9-yl group comprising a substituted or unsubstituted aromatic hydrocarbon group having ring carbon atoms of 6 to 50 at the 10th position thereof.

8. The biphenyl derivative according to any one of claims 1 to 3, which is a host material for an organic electroluminescent device.

9. An organic electroluminescent device, comprising:
at least one organic thin film layer comprising a light emitting layer sandwiched between a pair of electrodes consisting of an anode and a cathode,
wherein the organic thin film layer comprises, singly or as a component of a mixture, at least one compound selected from the group consisting of the biphenyl derivatives as claimed in claim 1.

10. The organic electroluminescent device according to claim 9, wherein, the light emitting layer comprises the biphenyl derivatives represented by the general formula (I) singly or as a component of a mixture.

11. The organic electroluminescent device according to claim 10, wherein, the light emitting layer comprises the biphenyl derivatives represented by the general formula (I) as a main component.

12. The organic electroluminescent device according to claim 9, wherein, the light emitting layer further comprises an arylamine compound.

13. The organic electroluminescent device according to claim 12, wherein, the arylamine compound is represented by general formula (A)

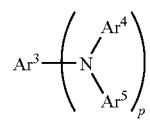

(A)

wherein $Ar^3$ represents a group selected from a phenyl group, a biphenyl group, a terphenyl group, a stilbene group and a distyrylaryl group,
$Ar^4$ and $Ar^5$ each represents a hydrogen atom, an aromatic hydrocarbon group having carbon atoms of 6 to 20, and $Ar^3$, $Ar^4$ and $Ar^5$ may have substituent, and
p represents an integer of 1 to 4.

14. The organic electroluminescent device according to claim 9, wherein, the light emitting layer further comprises a styrylamine compound.

15. The organic electroluminescent device according to claim 14, wherein, the styrylamine compound is represented by general formula (B)

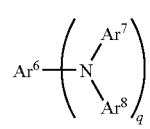

(B)

wherein $Ar^6$ to $Ar^8$ each represents a substituted or unsubstituted aryl group having ring carbon atoms of 6 to 40, and
q represents an integer of 1 to 4.

16. The biphenyl derivative according to claim 1, wherein at least two of $Ar^1$ to $Ar^3$ represent a substituted anthracene-9-yl group.

17. The biphenyl derivative according to claim 1, wherein each of $Ar^1$ to $Ar^3$ represent a substituted anthracene-9-yl group.

18. The biphenyl derivative according to claim 1, wherein $Ar^1$ and $Ar^2$ each independently represent a 9-phenanthryl group, a 9-anthryl group, or a 1-pyrenyl group.

19. The biphenyl derivative according to claim 1, wherein $Ar^3$ represents a unsubstituted phenyl group, a 1-naphthyl group, a 2-naphtyl group, a 9-phenanthryl group, a 9-anthryl group, or a 1-pyrenyl group.

* * * * *